(12) United States Patent
Leibel et al.

(10) Patent No.: US 7,339,028 B2
(45) Date of Patent: Mar. 4, 2008

(54) MAHOGANOID POLYPEPTIDES, AND RELATED COMPOSITIONS AND METHODS

(75) Inventors: Rudolph L. Leibel, New York, NY (US); Wendy K. Chung, Hackensack, NJ (US); Loan K. Phan, Brooklyn, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 374 days.

(21) Appl. No.: 10/456,881

(22) Filed: Jun. 6, 2003

(65) Prior Publication Data

US 2004/0053303 A1 Mar. 18, 2004

Related U.S. Application Data

(60) Provisional application No. 60/386,784, filed on Jun. 6, 2002.

(51) Int. Cl.
*C07K 14/435* (2006.01)
*C07H 21/00* (2006.01)

(52) U.S. Cl. .................. 530/350; 536/23.1; 536/23.5; 435/69.1

(58) Field of Classification Search .................. None
See application file for complete search history.

(56) References Cited

U.S. PATENT DOCUMENTS 6,001,619 A 12/1999 Beach et al.
2005/0196754 A1* 9/2005 Drmanac et al. ............... 435/6

OTHER PUBLICATIONS

Database UniProt_05.80, Accession No. Q9D074, public availability date Jun. 1, 2001.*
Database PIR_80, Accession No. T19204, public availability date Oct. 15, 1999.*
Database UniProt_05.80, Accession No. O60291, public availability date Aug. 1, 1998.*
Borden, K.L.B., et al. (1996) The RING finger domain: a recent example of a sequence-structure family, *Current Opinion in Structural Biology* 6:395-401 (Exhibit 1).
Bahary, N., et al. (1993) Microdissection of proximal mouse Chromosome 6: identification of RFLPs tightly linked to the *ob* mutation, *Mammalian genome* 4:511-515 (Exhibit 2).
Bultman, S.J., et al. (1993) Molecular Characterization of the Mouse Agouti Locus, *Cell* 71:1195-1204 (Exhibit 3).
Bronson, R.T., et al. (2001) Mice with Mutations in the Mahogany Gene *Atrn* Have Cerebral Spongiform Changes, *Journal of Neuropathology and Experimental Neurology* 60:724-730 (Exhibit 4).
Conaway, R.C., et al. (2002) Emerging Roles of Ubiquitin in Transcription Regulations, *Science* 296:1254-1258 (Exhibit 5).
Chung, W.K., et al. (1997) Exonic and Intronic Sequence Variation in Human Leptin Receptor Gene (LEPR), *Diabetes* 46:1509-1511 (Exhibit 6).

Dinulescu, D.M., et al. (1998) *Mahogany (mg)* stimulates feeding and increases basal metabolic rate independent of its suppression of *agouti*, *Proc. Natl. Acad. Sci. USA* 95:12707-12712 (Exhibit 7).
Francke, S., et al. (2001) A genome-wide scan for coronary heart disease suggests in Indo-Mauritians a suspectibility locus on chromosome 16p13 and replicates linkage with the metabolic syndrome on 3q27, *Human Molecular Genetics* 10:2751-2765 (Exhibit 8).
Gunn, T.M., et al. (1999) The mouse *mahogany* locus encodes a transmembrane form of human attractin, *Nature* 398:152-156 (Exhibit 9).
Gunn, T.M., et al. (2001) Molecular and Phenotypic Analysis of *Attractin* Mutant Mice, *Genetics* 158:1683-1695 (Exhibit 10).
Haskell-Luevano, C. (2001) Agouti-related protein functions as an inverse agonist at a constitutively active brain melanocortin-4 receptor, *Regulatory Peptides* 99:1-7 (Exhibit 11).
He, L., et al. (2001) A biochemical function for attractin in agouti-induced pigmentation and obesity, *Nature Genetics* 27:40-47 (Exhibit 12).
He, L., et al. (2003) Spongiform Degeneration in *mahoganoid* Mutant Mice, *Science* 299:710-712 (Exhibit 13).
Joazeiro, C.A.P., et al. (2000) RING Finger Proteins: Mediators of Ubiquitin Ligase Activity, *Cell* 102:549-552 (Exhibit 14).
Kuramoto, T., et al. (2001) Attractin/Mahogany/Zitter plays a critical role in myelination of the central nervous system, *PNAS* 98:559-564 (Exhibit 15).
Kwon, Y.T., et al. (2001) Construction and Analysis of Mouse Strains Lacking the Ubiquitin Ligase UBR1 (E3α) of the N-End Rule Pathway, *Molecular and Cellular Biology* 21:8007-8021 (Exhibit 16).
Lane, P.W. (1960) New Mutants, *Mouse News Letter* 22: 35-36 (Exhibit 17).
Lane, P.W., et al. (1960) Mahogany, a Recessive Color Mutation in Linkage Group V of the Mouse, *J. Hered.* 51:228-230 (Exhibit 18).
Leibel, R.L., et al. (1997) The Molecular Genetics of Rodent Single Gene Obesities, *The Journal of Biological* Chemistry 272:31937-31940 (Exhibit 19).
Layfield, R., et al. (2001) The ubiquitin protein catabolic disorders, *Neuropathology and Applied Neurobiology* 27:171-179 (Exhibit 20).
Löwer, R. (1999) The pathogenic potential of endogenous retroviruses: facts and fantasies, *Trends in Microbiology* 7:350-356 (Exhibit 21).
Miller, M.W., et al. (1993) Cloning of the mouse *agouti* gene predicts a secreted protein ubiquitously expressed in mice carrying the *lethal yellow* mutation, *Genes and Development* 7:454-467 (Exhibit 22).
Miller, K.A., et al. (1997) Genetic Studies of the Mouse Mutations *mahogany* and *mahoganoid*, *Genetics* 146:1407-1415 (Exhibit 23).
Michaud, E.J., et al. (1994) A molecular model for the genetic and phenotypic characteristics of the mouse lethal yellow ($A_y$) mutation, *Proc. Natl. Acad. Sci. USA* 91:2562-2566 (Exhibit 24).

(Continued)

Primary Examiner—Eileen B. O'Hara
(74) Attorney, Agent, or Firm—John P. White; Cooper & Dunham LLP

(57) ABSTRACT

This invention provides an isolated mahoganoid polypeptide. This invention also provides an isolated mahoganoid nucleic acid, as well as related nucleic acids, pharmaceutical compositions, antibodies, assay methods, therapeutic methods and articles of manufacture.

2 Claims, 12 Drawing Sheets

OTHER PUBLICATIONS

Nagle, D.L., et al. (1999) The *mahogany* protein is a receptor involved in suppression of obesity, *Nature* 398:148-152 (Exhibit 25).

Nijenhuis, W.A.J., et al. (2001) AgRP (83-132) Acts as an Inverse Agonist on the Human-Melanocortin-4 Receptor, *Molecular Endocrinology* 15:164-171 (Exhibit 26).

Nagase, T., et al. (1998) Prediction of the Coding Sequences of Unidentified Human Genes. IX. The Complete Sequences of 100 New cDNA Clones from Brain Which Can Code for Large Proteins in vitro, *DNA Research* 5:31-39 (Exhibit 27).

Ollmann, M.M., et al. (1997) Antagonism of Central Melanocortin Receptors in Vitro and in Vivo by Agouti-Related Protein, *Science* 278:135-137 (Exhibit 28).

Pfaffl, M.W., et al. (2002) Real-time RT-PCR quantification of insulin-like growth factor (IGF)-1, IGF-1 receptor, IGF-2, IGF-2 receptor, insulin receptor, growth hormone receptor, IGF-binding proteins 1, 2 and 3 in the bovine species, *Domestic Animal Endocrinology* 22:91-102 (Exhibit 29).

Palmiter, R.D., et al. (1998) Life Without Neuropeptide Y, *Recent Progress in Hormone Research* 53:163-199 (Exhibit 30).

Roderick, T.H., et al. (1976) Chromosome 16 and mahoganoid (md), *Mouse News Letter* 55:16-18 (Exhibit 31).

Saurin, A.J., et al. (1996) Does this have a familiar RING?, *TIBS* 21:208-214 (Exhibit 32).

Seperack, P.K., et al. (1995) Retroviral sequences located within an intron of the d*ilute* gene alter d*ilute* expression in a tissue-specific manner, *The EMBO Journal* 14:2326-2332 (Exhibit 33).

Venter, J.C., et al. (2001) The Sequence of the Human Genome, *Science* 291:1304-1351 (Exhibit 34).

Weissman, A.M. (2001) Themes and Variation of Ubiquitylation, *Molecular Cell Biology* 2:169-178 (Exhibit 35).

Wolff, G.L., et al. (1978) Phaeomelanin synthesis and obesity in mice, *The Journal of Heredity* 69:295-298 (Exhibit 36).

Yeo, G.S.H., et al. (2000) The role of melanocortin signaling in the control of body weight: evidence from human and murine genetic models, *Q.J. Med.* 93:7-14 (Exhibit 37); and.

Zheng, N., et al. (2000) Structure of a c-Cb1-UbcH7 Complex: RING Domain Function in Ubiquitin-Protein Ligases, *Cell* 102:533-539 (Exhibit 38).

Phan, L. K. et al. The mouse mahoganoid coat color mutation disrupts a novel C3CH4 RING domain protein. The Journal of Clinical Investigation, vol. 110, No. 5, 1449-1459 (2002); (Exhibit 2).

He, L. et al. Spongiform degeneration in mahoganoid mutant mice. Science Proteins: Structure, Function, and Genetics, vol. 229, 710-712 (2003); (Exhibit 3) and.

International Search Report, Sep. 14, 2004 from the International Search Authority on International Application No. PCT/US03/18138 (Exhibit 4).

\* cited by examiner

FIGURE 8

ENSMUSP00000023159 (Mouse)

MGGEKFDTPHPEGYLFGENMDLNFLGSRPVQFPYVTPAPHEPVKTLRSLVNIRKDSLRLVRYKE
DADSPTEDGEKPRVLYSLEFTFDADARVAITIYCQAVEELVNGVAVYSCKNPSLQSETVHYKRG
VSQQFSLPSFKIDFSEWKDDELNFDLDRGVFPVVIQAVVDEGDVVEVTGHAHVLLAAFEKHVDG
SFSVKPLKQKQIVDRVSYLLQEIYGIENKNNQETKPSDDENSDNSSECVVCLSDLRDTLILPCR
HLCLCTSCADTLRYQANNCPICRLPFRALLQIRAVRKKPGALSPISFSPVLAQSVDHDEHSSSD
SIPPGYEPISLLEALNGLRAVSPAIPSAPLYEEITYSGISDGLSQASCPLAGLDRIMESGLQKG
KTQSKSPDSTLRSPSFPIHEEDEEKLSEDSDAPLPPSGVELVLRESSSPESFGTEEGDEPSLKQ
GSRVPSIDDVLQDGSPQHHGCSQPVPPADIYLPALGPESCSVGIEE

ENSP00000307460 (Human)

MGGEKFDTPHPEGYLFGENMDLNFLGSRPVQFPYVTPAPHEPVKTLRSLVNIRKDSLRLVRYKD
DADSPTEDGDKPRVLYSLEFTFDADARVAITIYCQASEEFLNGRAVYSPKSPSLQSETVHYKRG
VSQQFSLPSFKIDFSEWKDDELNFDLDRGVFPVVIQAVVDEGDVVEVTGHAHVLLAAFEKHMDG
SFSVKPLKQKQIVDRVSYLLQEIYGIENKNNQETKPSDDENSDNSNECVVCLSDLRDTLILPCR
HLCLCTSCADTLRYQANNCPICRLPFRALLQIRAVRKKPGALSPVSFSPVLAQSLEHDEHSNSD
SVPPGYEPISLLEALNGLRAVSPAIPSAPLYEEITYSGISDGLSQASCPLAAIDHILDSSRQKG
RPQSKAPDSTLRSPSSPIHEEDEEKLSEDVDAPPPLGGAELALRESSSPESFITEEVDESSSPQ
QGTRAASIENVLQDSSPEHCGRGPPADIYLPALGPDSCSVGIDE

```
Mouse BAB27816:      CVVCLSDL-RDTLILPCRHLCLCTSCADTLRYQ--ANNCPIC
Human KIAA0544:      CVVCLSDL-RDTLILPCRHLCLCTSCADTLRYQ--ANNCPIC
D.melanogaster AAF48305: CVICMSET-RDTLILPCRHLCLCNSCADSLRYQ--ANNCPIC
C.elegans CAA94116:  CIICLSDI-RDTVILPCRHLCVCSNCADSLRYK--HNNCPIC
Smart00184 RING:     CPICLEEYLKDPVVLPCGHT-FCRSCIRKWLESSNSNTCPIC
                      *    *     *  *   *    *          * *
```

US 7,339,028 B2

MAHOGANOID POLYPEPTIDES, AND RELATED COMPOSITIONS AND METHODS

This application claims priority of provisional application U.S. Ser. No. 60/386,784, filed Jun. 6, 2002, the contents of which are incorporated herein by reference.

The invention described herein was made with government support under NIH Grants DK-52431 and DK-26687. Accordingly, the United States government has certain rights in this invention.

Throughout this application, various references are cited. Disclosure of these references in their entirety is hereby incorporated by reference into this application to more fully describe the state of the art to which this invention pertains.

BACKGROUND OF THE INVENTION

Molecular cloning of the five extant monogenic forms of rodent obesity identified critical molecules in the pathways regulating energy homeostasis in animals and human (1). The agouti (a) gene encodes a 131 amino acid peptide, agouti signaling protein (ASP) that is normally secreted only in the follicular cells of the dermal papilla of the skin (2-4). Mutations of agouti (e.g. $A^y$ and $A^{vy}$) that cause ectopic overexpression of ASP in the hypothalamus and skin, result in a pleiotropic syndrome that includes increased lean and adipose tissue, yellow pelage (coat), hyperinsulinemia, hyperphagia, and hyperglycemia (3-5). ASP antagonizes the binding of alpha-melanocortin stimulating hormone (α-MSH) to the melanocortin 1 receptor (MC1R) causing melanogenesis to switch from the production of black/brown pigment (eumelanin) to a yellow/red pigment (pheomelanin) (FIG. 1) (2). In the hypothalamus, agouti related protein (AgRP) is the natural antagonist of MC3R and MC4R. AgRP also acts as an inverse agonist at MC4R in both human and mouse (6, 7). In $A^y$ mice, ectopically produced ASP competes with α-MSH for binding to MC3R and MC4R, resulting in hyperphagia, increased body fat, and disordered insulin homeostasis (8).

Two other mutations, mahogany ($Atrn^{mg}$, Chr 2) and mahoganoid (md, Chr 16), affect coat color and body weight. Both mutations are unique in their ability to suppress the obesity and darken the coat (umbrous effect) caused by mutations resulting in the ectopic overexpression of ASP. There are three reported alleles of mahogany: $Atrn^{mg}$, $Atrn^{mg-L}$, and $Atrn^{mg-3J}$ that are coisogenic on mouse strains LDJ/Le, C3H/HeJ, and C3HeB/FeJ, respectively (9, 10). $Atrn^{mg}$ and $Atrn^{mg-L}$ are each the result of ~5 kb retrovirus insertions in introns 26 and 27, respectively, that disrupt the splicing of Atrn. $Atrn^{mg-3J}$ has a 5-bp deletion at nucleotide 2,809 introducing a stop codon that results in a severely truncated protein. Attractin (Atrn) encodes a single-pass transmembrane ~210 kDa protein containing 3 epidermal growth factor (EGF) domains, two laminin-like EGF repeats, a CUB domain, two plexin-like repeats, a C-type lectin and seven consecutive Kelch repeats (9, 10). The predicted structure of ATRN suggests that it functions as a receptor or receptor-like protein. The $Atrn^{mg}$ mutation does not suppress the obese phenotype of Mc4r null mice, or that of several monogenic obese models ($Lepr^{db}$, $Lep^{ob}$, tub, $Cpe^{fat}$) (9, 10), but does suppress diet-induced obesity (10). Homozygosity for LDJ/Le $Atrn^{mg}$ backcrossed for 6-8 generations onto a C57BL/6J background suppresses $A^y$-induced weight gain by increasing basal metabolic rate (11). In animals doubly mutant for mg and $A^y$, food intake is not reduced relative to controls (+/+ $A^y$/a and mg/mg a/a), but body weight is reduced due to higher metabolic rate (11). Mahogany mice are not hyperphagic on a C3H/HeJ background (12). Homozygous $Atrn^{mg}$ animals develop abnormal myelination and vacuolization throughout the brain and spinal cord in association with severe tremors and flaccid paresis (13). The tremors may account for the increased metabolic rate. The neuropathological changes characteristic of $Atrn^{mg}$ animals, and the specificity of binding of ASP but not AgRP to ATRN (14), make it unlikely that ATRN plays a specific role in hypothalamic control of energy homeostasis aside from its effects on muscle motor activity.

Md has effects on coat color and obesity in $A^y$ mice that are analogous to $Atrn^{mg}$. The md mutation originally arose spontaneously in the C3H/HeJ strain at Jackson Laboratory in the early 1960s. Subsequently, four additional spontaneous mutations ($md^{2J}$, $md^{4J}$, $md^{5J}$, and $md^{6J}$) have been documented at this locus Like $Atrn^{mg}$, mahoganoid darkens the back, ears, and tail of nonalbino mice (15, 16) This darkening effect is described as an "umbrous" coat. Md suppresses $A^y$-induced yellow pigmentation and $A^y$-induced obesity in a gene dose-dependent manner (17) Similar to $Atrn^{mg}$ on the C57BL/6J background, homozygosity for md on the C3H/HeJ background causes hyperphagia (11). The ability of md to induce hyperphagia suggests that the md gene product has effects on energy homeostasis distinct from epistatic effects in the context of overexpression of ASP ($A^y$) Genetic studies have positioned md, functionally, at the same level or upstream of MC1R and downstream of ASP based on findings that the $Mc1r^e$ mutation (extension, resulting in a yellow coat) suppressed the coat color effect of md, and that md suppressed both the yellow and obese phenotypes of $A^y$ mice (17) (FIG. 1). Linkage analysis positioned md on chromosome 16, about 2 cM from the centromere (18, 19) Identification of md and its function could provide additional insight into the control of melanocortin signaling.

SUMMARY OF THE INVENTION

This invention provides an isolated mahoganoid polypeptide, or a portion thereof having ubiquitin ligase activity.

This invention also provides an isolated nucleic acid encoding a mahoganoid polypeptide, or a portion thereof having ubiquitin ligase activity.

This invention also provides a replicable vector comprising an isolated nucleic acid encoding a mahoganoid polypeptide, or a portion thereof having ubiquitin ligase activity.

This invention also provides an isolated nucleic acid that specifically hybridizes to mahoganoid polypeptide-encoding mRNA.

This invention also provides a host-vector system comprising a cell having therein a replicable vector comprising a nucleic acid encoding a mahoganoid polypeptide, or a portion thereof having ubiquitin ligase activity.

This invention also provides an antibody which specifically binds to an isolated mahoganoid polypeptide, or a portion thereof having ubiquitin ligase activity.

This invention also provides a composition of matter comprising an isolated nucleic acid encoding a mahoganoid polypeptide, or a portion thereof having ubiquitin ligase activity and a pharmaceutically acceptable carrier.

This invention also provides a composition of matter comprising an isolated mahoganoid polypeptide, or a portion thereof having ubiquitin ligase activity and a pharmaceutically acceptable carrier.

This invention also provides a composition of matter comprising an isolated nucleic acid that specifically hybridizes to mahoganoid polypeptide-encoding mRNA and a pharmaceutically acceptable carrier.

This invention also provides a method for decreasing the amount of mahoganoid polypeptide in a cell comprising contacting the cell with an agent that specifically inhibits mahoganoid polypeptide expression in the cell, thereby decreasing the amount of mahoganoid polypeptide in the cell.

This invention also provides a method for decreasing the amount of mahoganoid polypeptide in a subject's cells comprising administering to the subject an agent that specifically inhibits mahoganoid polypeptide expression in a cell, thereby decreasing the amount of mahoganoid polypeptide in the subject's cells.

This invention also provides a method for treating an overweight subject comprising administering to the subject a therapeutically effective amount of an agent that specifically inhibits mahoganoid polypeptide expression in a cell, thereby treating the subject.

This invention also provides a method for inhibiting the onset of weight gain in a subject comprising administering to the subject a prophylactically effective amount of an agent that specifically inhibits mahoganoid polypeptide expression in a cell, thereby inhibiting the onset of weight gain in the subject.

This invention also provides an article of manufacture comprising a packaging material having therein an agent that specifically inhibits mahoganoid polypeptide expression in a cell, and a label indicating a use for the agent in treating an overweight subject and/or inhibiting the onset of weight gain in a subject.

This invention also provides a method for determining whether an agent decreases mahoganoid polypeptide expression in a cell, which method comprises the steps of
  (a) contacting the cell with the agent under suitable conditions;
  (b) determining the amount of mahoganoid polypeptide expression in the cell after a suitable period of time; and
  (c) comparing the amount of mahoganoid polypeptide expression determined in step (b) with the amount of mahoganoid polypeptide expression in a cell in the absence of the agent, whereby a lower amount of mahoganoid polypeptide expression in the cell contacted with the agent, relative to the amount of expression in the absence of the agent, indicates that the agent decreases mahoganoid polypeptide expression in the cell.

This invention also provides a method for determining whether an agent inhibits the ubiquitin ligase activity of mahoganoid polypeptide, which method comprises the steps of
  (a) contacting mahoganoid polypeptide and ubiquitin with the agent under conditions which would permit mahoganoid polypeptide ubiquitin ligase activity in the absence of the agent;
  (b) determining the amount of ubiquitin ligated after a suitable period of time; and
  (c) comparing the amount of ligated ubiquitin determined in step (b) with the amount of ligated ubiquitin in the absence of the agent, whereby a lower amount of ligated ubiquitin in the presence of the agent, relative to the amount of ligated ubiquitin in the absence of the agent, indicates that the agent inhibits the ubiquitin ligase activity of mahoganoid polypeptide.

This invention also provides a method for increasing the amount of mahoganoid polypeptide in a cell comprising contacting the cell with an agent that specifically increases mahoganoid polypeptide expression in the cell, thereby increasing the amount of mahoganoid polypeptide in the cell.

This invention also provides a method for increasing the amount of mahoganoid polypeptide in a subject comprising administering to the subject an agent that specifically increases mahoganoid polypeptide expression in a cell, thereby increasing the amount of mahoganoid polypeptide in the subject.

This invention also provides a method for treating an underweight subject comprising administering to the subject a therapeutically effective amount of an agent that specifically increases mahoganoid polypeptide expression in a cell, thereby treating the subject.

This invention also provides a method for inhibiting the onset of weight loss in a subject comprising administering to the subject a prophylactically effective amount of an agent that specifically increases mahoganoid polypeptide expression in a cell, thereby inhibiting the onset of weight loss in the subject.

This invention also provides an article of manufacture comprising a packaging material having therein an agent that specifically increases mahoganoid polypeptide expression in a cell, and a label indicating a use for the agent in treating an underweight subject and/or inhibiting the onset of weight loss in a subject.

This invention also provides a method for determining whether an agent increases mahoganoid polypeptide expression in a cell, which method comprises the steps of
  (a) contacting the cell with the agent under suitable conditions;
  (b) determining the amount of mahoganoid polypeptide expression in the cell after a suitable period of time; and
  (c) comparing the amount of mahoganoid polypeptide expression determined in step (b) with the amount of mahoganoid polypeptide expression in a cell in the absence of the agent, whereby a higher amount of mahoganoid polypeptide expression in the cell contacted with the agent, relative to the amount of expression in the absence of the agent, indicates that the agent increases the amount of mahoganoid polypeptide expression in the cell.

Finally, this invention provides a method for determining whether an agent increases the ubiquitin ligase activity of mahoganoid polypeptide, which method comprises the steps of
  (a) contacting mahoganoid polypeptide and ubiquitin with the agent under conditions which would permit mahoganoid polypeptide ubiquitin ligase activity in the absence of the agent;
  (b) determining the amount of ligated ubiquitin after a suitable period of time; and
  (c) comparing the amount of ligated ubiquitin determined in step (b) with the amount of ligated ubiquitin in the absence of the agent, whereby a higher amount of ligated ubiquitin in the presence of the agent, relative to the amount of ligated ubiquitin in the absence of the agent, indicates that the agent increases the ubiquitin ligase activity of mahoganoid polypeptide.

Figures 1A, 1B:
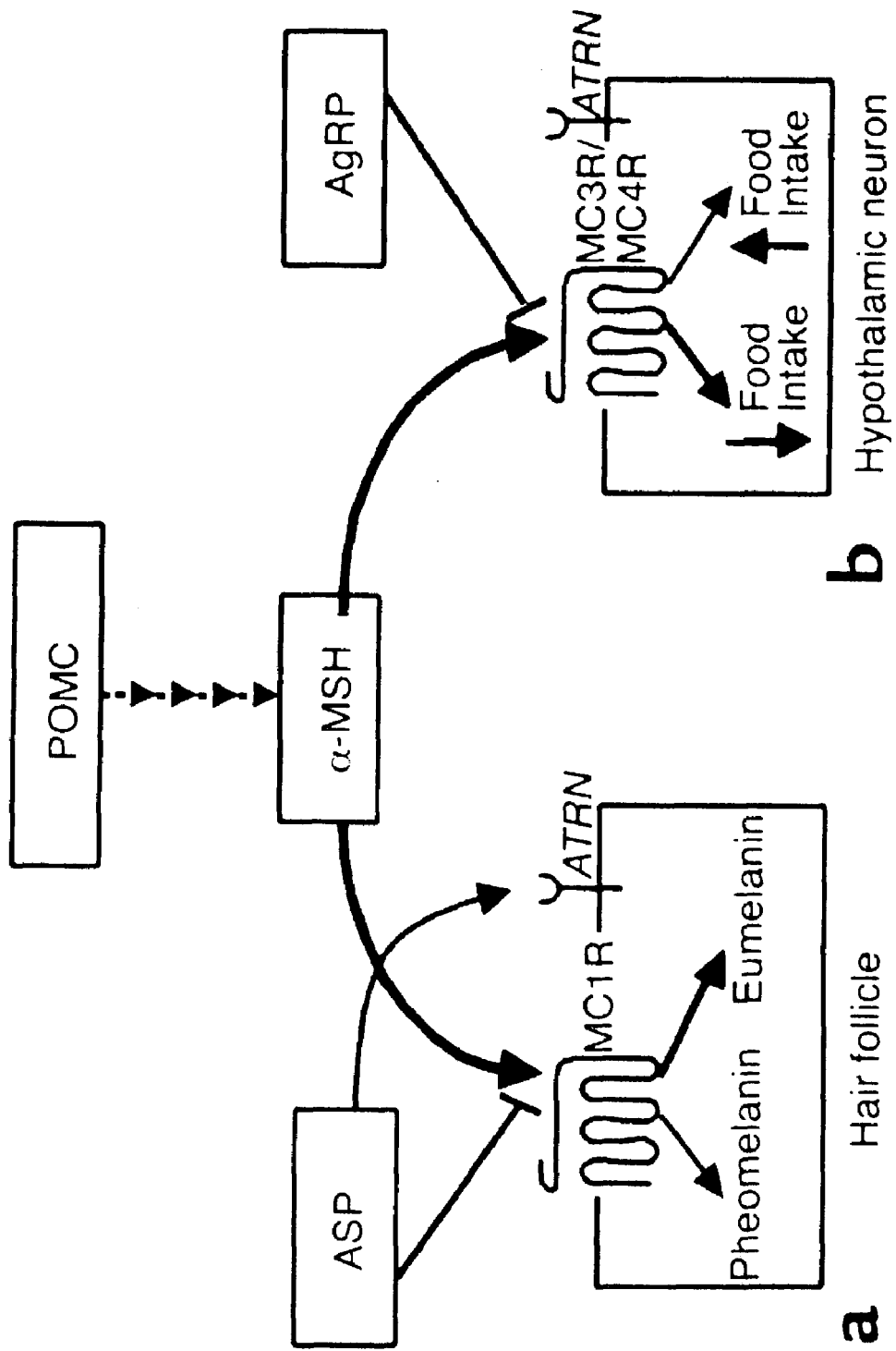
FIGS. 1A and 1B

Schematic of melanocortin signaling pathways, specifically melanocortin signaling in the hair follicle and hypothalamus. α-MSH is a melanocortin peptide that is cleaved from the pro-opiomelanocortin precursor (POMC). (A)

α-MSH acts on MC1R resulting in an increase in cAMP to darken coat color. Agouti signaling protein (ASP) antagonizes α-MSH binding at MC1R resulting in pheomelanin synthesis. ATRN (mahogany) may function to down-regulate or desensitize MC1R or may be involved in ASP processing or binding to MC1R. (B) α-MSH activates MC4R to decrease food intake and increase energy expenditure. AgRP competes with α-MSH for binding at MC4R/MC3R resulting in increased food intake. $A^y$ mice ectopically over-produce ASP, interfering with α-MSH signaling at MC4R/MC3R and resulting in an obese phenotype due to increased food intake.

FIG. 2

Coat colors. C57BL/6J +/+ $A^y$/a and C57BL/6J +/+ a/a mice have yellow and black pelage, respectively. Homozygosity for md results in a darkened pelage in Agouti (A/?) animals, whereas heterozygous md/+ animals have normal agouti (alternate black, yellow banding) pelage. Colors are not shown in the Figure.

FIG. 3

Genetic map of region of proximal Chr. 16 containing md. Map is based on 149 progeny of a B6.C3H-md-A md/md, A/?×B6.C3H-md-A md/+, A/? cross. The congenic C3H/HeJ interval is indicated. Genotype at md is inferred by coat color. md/md A/? animals are umbrous (mahoganoid), md/+ A/? are agouti.

FIGS. 4A-4C

Genetic and physical maps of md minimal interval. (A) Genetic map of proximal chromosome 16. Distances between markers indicated in centiMorgans. (B) Mouse genomic clones spanning the minimal interval containing md. Distances indicated are in megabases. (C) Locations of all transcripts (identified by accession number) and predicted genes (all mCGs). Riken full-length cDNA AK011747 is the Mahoganoid transcript (2010 bp).

FIGS. 5A-5C

PCR amplification and Southern blot analyses of md alleles. (A) PCR amplification of exon 12 from genomic DNA from all md alleles produces a ~0.5 kb fragment except for $md^{2J}$. (B) Southern blot of Pst I digest of md allelic series (md, $md^{2J}$, $md^{4J}$, $md^{5J}$, $md^{6J}$) genomic DNA probed with part of exon 12 and its 5' intronic region. The $md^{2J}$ revealed a new fragment of 0.7 kb and a lack of fragment 1.4 kb corresponding to exon 12 whereas md showed a loss of 1.1 kb fragment and a novel 0.6 kb fragment corresponding to the intronic region 5' of exon 12. $md^{4J}$, $md^{5J}$ and $md^{6J}$ showed fragments of similar size to the C3H/HeJ +/+ control. (C) Southern blot of Hind III digest of md allelic series probed with cDNA for exons 2-9 shows novel restriction site in $md^{5J}$.

FIG. 6

Restriction map and location/nature of mahoganoid mutations. (top) Restriction map of normal fragment sizes. (bottom) md, $md^{2J}$, and $md^{5J}$ mutations are all due to retroviral insertions. $md^{5J}$ and md are due to ~5 kb insertion located in the intronic region 3' of exon 2 and 5' of exon 12, respectively. $md^{2J}$ is due to ~8 kb insertion within exon 12. Fragment sizes shown above the inserted sequences represent the sizes from the new restriction sites located within retrovirus insertion to the normal restriction site in the direction of the arrow. RF indicates the location of the RING Finger domain located in exon 10. GenBank numbers for md with retrovirus insertions are indicated in parentheses adjacent to new sequences (SEQ ID Nos: 1-6). IAP denotes mouse retrovirus-like repetitive interacisternal type A particle. Sequences in bold are normal sequences. The inserted sequences are underline.

Figure 7A:
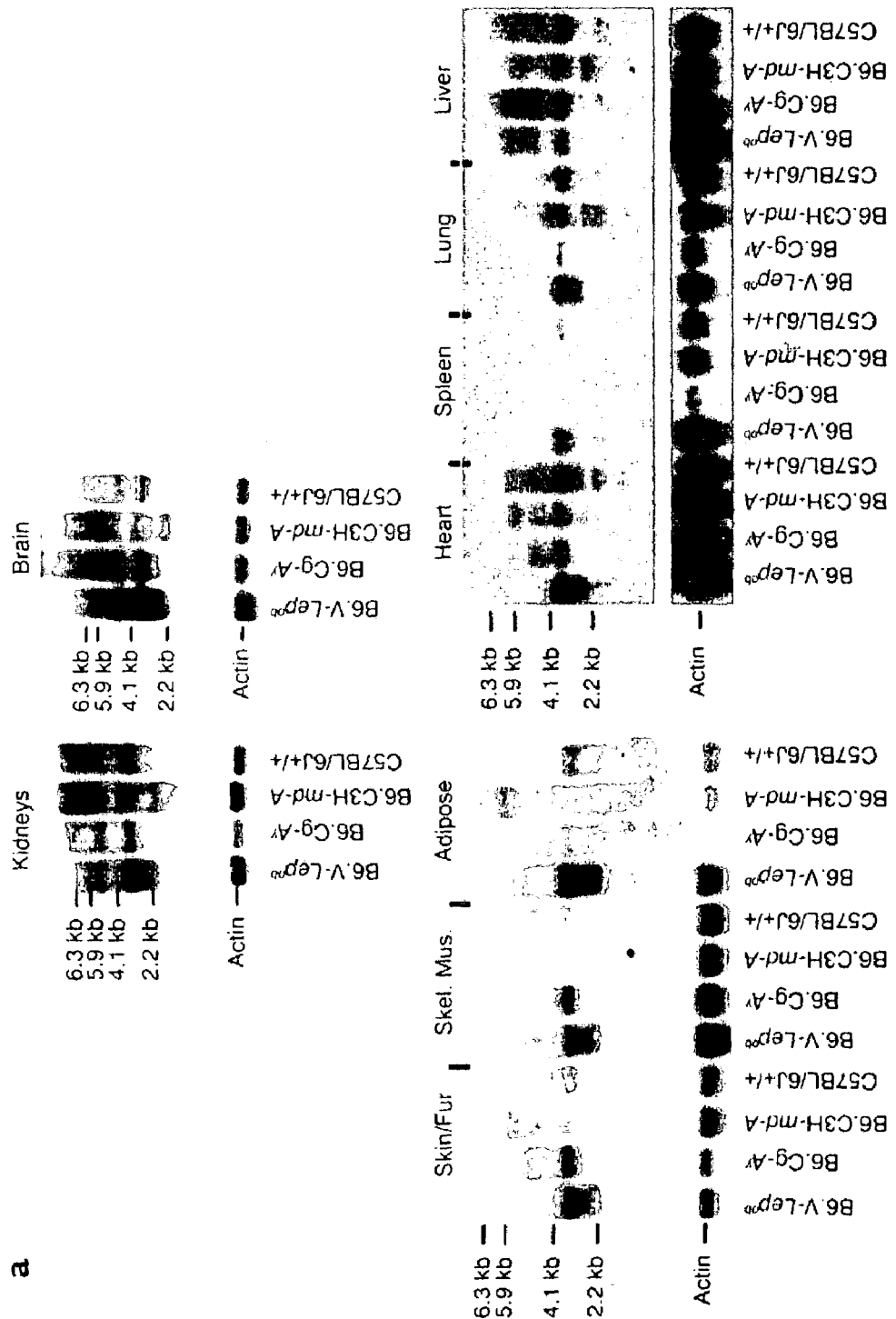
Figure 7B:
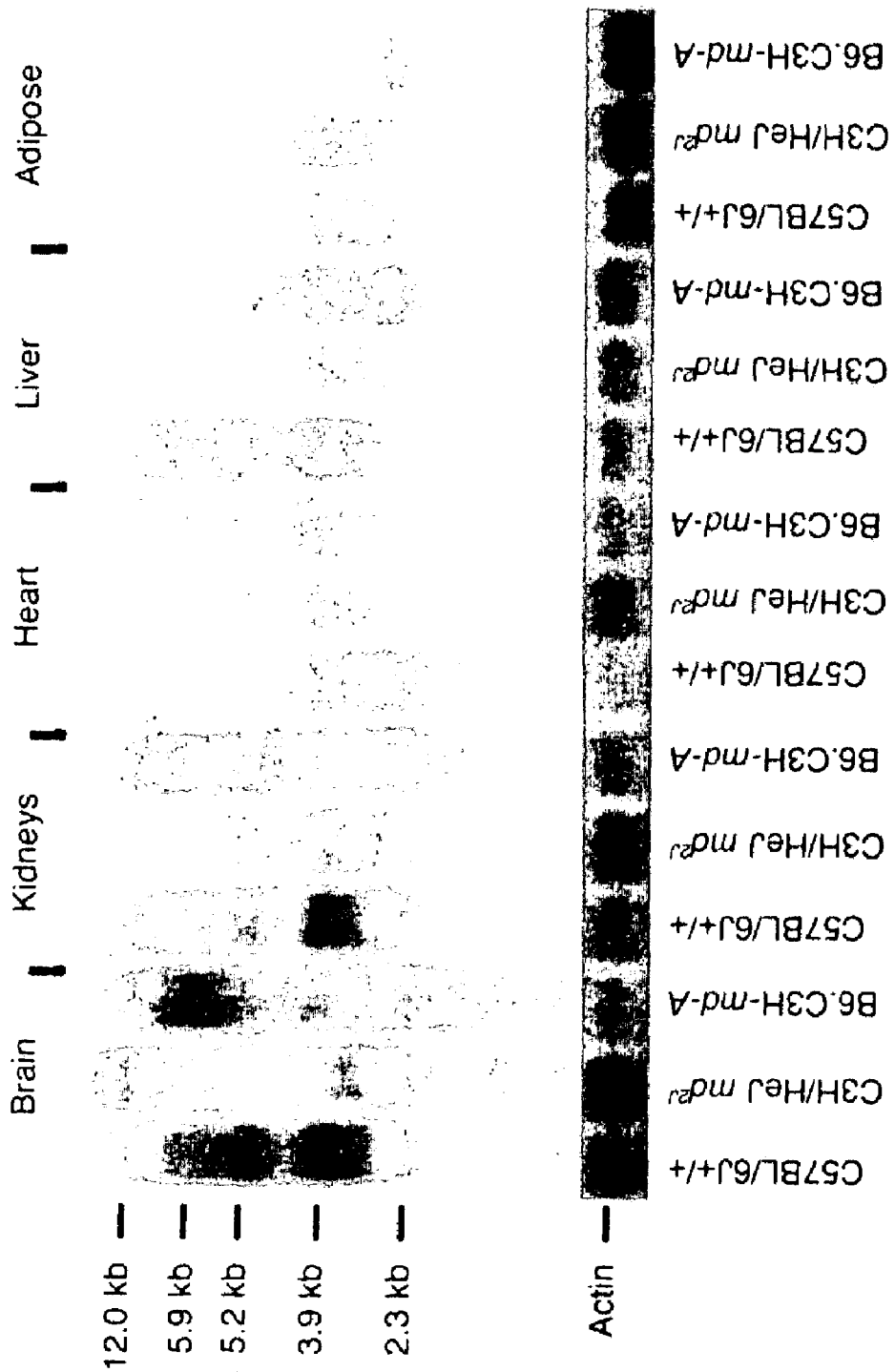

FIGS. 7A and 7B

Northern Blots. (A) mahoganoid 3.9 kb transcript is expressed in all tissues tested. A 5.2 kb transcript is also seen in brain, kidneys, and liver. Only kidney showed a faint transcript of 1.9 Kb. (B) The retrovirus insertion in md and $md^{2J}$ produces several aberrantly sized transcripts: 5.9 kb/5.5 kb/4.1 kb/2.2 kb in md and 12.0 kb/3.6 kb in $md^{2J}$.

FIG. 8

Mahoganoid protein (BAB27816). 494 amino acids (SEQ ID NO: 7) containing a C3HC4 RING finger domain (underlined) (SEQ ID NO: 9). Amino acid comparison of md RING domain with Smart00184 (c-Cbl) (SEQ ID NO: 13) and other proteins that have E3 ubiquitin-protein ligase activity (33), suggesting a general function of this domain. Human (KIAA0544) (SEQ ID NO: 10), D. melanogaster (AAF48305) (SEQ ID NO. 11), C. elegans (CAA94116) (SEQ ID NO: 12) homologs of mouse mahoganoid have the conserved C3HC4 RING finger. Conserved amino acids are bold. * indicates the conserved cysteine and histidine residues found in all C3HC4 RING finger domains (34).

FIG. 9

Three potential models for Mahoganoid biological effects. Mahoganoid may decrease signaling through MC1R or MC3R/MC4R by increasing expression or activity of an inverse agonist of MC1R or MC3R/MC4R; influencing the physical proximity or binding of ASP and AgRP to their receptors by influencing binding of ATRN to ASP; and decreasing the availability of α-MSH to its receptors through sequestration or turnover of α-MSH.

DETAILED DESCRIPTION OF THE INVENTION

Definitions

As used in this application, except as otherwise expressly provided herein, each of the following terms shall have the meaning set forth below.

"Administering" shall mean delivering in a manner which is effected or performed using any of the various methods and delivery systems known to those skilled in the art. Administering can be performed, for example, topically, intravenously, pericardially, orally, via implant, transmucosally, transdermally, intramuscularly, subcutaneously, intraperitoneally, intrathecally, intralymphatically, intralesionally, or epidurally. Administering can also be performed, for example, once, a plurality of times, and/or over one or more extended periods.

"Agent" shall mean any chemical entity, including, without limitation, a glycomer, a protein, an antibody, a lectin, a nucleic acid, a small molecule, and any combination thereof.

"Antibody" includes, by way of example, both naturally occurring antibodies (e.g., IgG, IgM, IgE and IgA) and non-naturally occurring antibodies. The term "antibody" also includes polyclonal and monoclonal antibodies, and antigen-binding fragments thereof (e.g., antigen-binding portions). Furthermore, the term "antibody" includes chimeric antibodies, wholly synthetic antibodies, human and humanized antibodies, and antigen-binding fragments thereof.

"Host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

"Increasing the ubiquitin ligase activity" of mahoganoid polypeptide includes, without limitation, increasing the rate at which such ligase activity occurs and/or altering the reaction equilibrium thereof so as to increase the amount of ligated ubiquitin once equilibrium is reached.

"Inhibiting the ubiquitin ligase activity" of mahoganoid polypeptide includes, without limitation, reducing the rate at which such ligase activity occurs and/or altering the reaction equilibrium thereof so as to reduce the amount of ligated ubiquitin once equilibrium is reached.

"Inhibiting the onset" of a disorder shall mean either lessening the likelihood of the disorder's onset, or preventing the onset of the disorder entirely. In the preferred embodiment, inhibiting the onset of a disorder means preventing its onset entirely.

"Isolated", as used herein, with respect to a particular polypeptide or nucleic acid, includes, without limitation, being in a milieu having a reduced amount of other polypeptides or nucleic acids, respectively. In one embodiment, an isolated polypeptide or nucleic acid is free of other polypeptides or nucleic acids, respectively. In another embodiment, an isolated subject polypeptide or nucleic acid is in a milieu containing other polypeptides or nucleic acids, respectively, in a total amount which does not exceed the amount of the subject polypeptide or nucleic acid, respectively.

"Mahoganoid polypeptide" and "mahoganoid protein" are used equivalently herein, and are characterized, inter alia, by having ubiquitin ligase activity. Mahoganoid polypeptide is exemplified by the human and mouse polypeptides having the sequences set forth in FIG. 8. Mahoganoid polypeptide, also referred to as "MD", is encoded by the mahoganoid gene, also referred to as "md", and includes all allelic variants thereof. The mahoganoid polypeptide-encoding gene is also referred to as "Mahogunin", "Mgn" and "MGN", and the mahoganoid polypeptide is also referred to as "MGN." On certain occasions, the term "mahoganoid" is used in the Experimental Details to refer to mutant mahoganoid genes and/or polypeptides. As used herein, a "mutant" mahoganoid polypeptide is a non-wild type mahoganoid polypeptide correlative with, for example, a change in coat color, body weight and/or brain anatomy and function. Except for this mutant-related usage in the Experimental Details, the meaning of which is clear from its context, mahoganoid polypeptide shall have the meaning as otherwise set forth in this application.

"Mammalian cells" include, without limitation, normal, abnormal and transformed mammalian cells, and are exemplified by neurons, epithelial cells, muscle cells, blood cells, immune cells, stem cells, osteocytes, endothelial cells and blast cells.

"Mammalian polypeptide" means a polypeptide originating from a mammalian cell.

The term "nucleic acid" refers to a polymer of deoxyribonucleotides and/or ribonucleotides. The deoxyribonucleotides and ribonucleotides can be naturally occurring or synthetic analogues thereof.

"Overweight subject" includes, without limitation, a subject whose weight exceeds the ideal weight for that subject by more than 20%. In one embodiment, the subject's weight exceeds the ideal weight by 50%, 100% or 200%.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

The terms "polypeptide" and "protein" are used interchangeably herein, and each means a polymer of amino acid residues. The amino acid residues can be naturally occurring or chemical analogues thereof. Polypeptides and proteins can also include modifications such as glycosylation, lipid attachment, sulfation, hydroxylation, and ADP-ribosylation.

"Prophylactically effective amount" means an amount sufficient to inhibit the onset of a disorder in a subject. Simple titration experiments can readily be performed by one of ordinary skill to determine such amount.

"Specifically bind" shall mean that, with respect to the binding of an antibody to its antigen, the antibody binds to the antigen with a greater affinity than that with which it binds to most other antigens. In the preferred embodiment, the antibody binds to the antigen with a greater affinity than that with which it binds to all other antigens.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression (a) more than the expression of any other protein, or (b) more than the expression of all but 10 or fewer other proteins.

As used herein, "subject" means any animal or artificially modified animal, such as a mammal or a bird, including, without limitation, a cow, a horse, a sheep, a pig, a dog, a cat, a rodent such as a mouse or rat, a chicken and a primate. In the preferred embodiment, the subject is a human.

"Suitable conditions" shall have a meaning dependent on the context in which this term is used. That is, when used in connection with contacting an agent to a cell, this term shall mean conditions that permit an agent capable of doing so to enter a cell and perform its intended function. In one embodiment, the term "suitable conditions" as used herein means physiological conditions.

"Therapeutically effective amount" means an amount sufficient to treat a subject. A person of ordinary skill in the art can perform simple titration experiments to determine such amount.

"Treating" means either slowing, stopping or reversing the progression of a disorder. As used herein, "treating" also means the amelioration of symptoms associated with the disorder.

"Underweight subject" includes, without limitation, a subject whose ideal weight exceeds his actual weight by more than 20%.

"Vector" shall mean any nucleic acid vector known in the art. Such vectors include, but are not limited to, plasmid vectors, cosmid vectors, and bacteriophage vectors. For example, one class of vectors utilizes DNA elements which are derived from animal viruses such as bovine papilloma virus, polyoma virus, adenovirus, vaccinia virus, baculovirus, retroviruses (RSV, MMTV, or MOMLV), Semliki Forest virus, SV40 virus or lentiviruses.

EMBODIMENTS OF THE INVENTION

This invention provides an isolated mahoganoid polypeptide, or a portion thereof having ubiquitin ligase activity. In one embodiment, the polypeptide is a mammalian polypeptide. In another embodiment, the polypeptide is a human polypeptide. In another embodiment, the polypeptide is a murine polypeptide.

This invention also provides an isolated nucleic acid encoding a mahoganoid polypeptide, or a portion thereof having ubiquitin ligase activity. In one embodiment, the nucleic acid is DNA. In another embodiment, the nucleic acid is genomic DNA. In another embodiment, the nucleic acid is cDNA. In a further embodiment, the nucleic acid is RNA.

In another embodiment of the invention, the nucleic acid is labeled with a detectable marker, such as a radioactive, a colorimetric, a luminescent or a fluorescent label.

This invention also provides a replicable vector comprising an isolated nucleic acid encoding a mahoganoid polypeptide, or a portion thereof having ubiquitin ligase activity. In further embodiments, the vector can be a plasmid, a cosmid, YAC or a λ phage.

This invention also provides an isolated nucleic acid that specifically hybridizes to mahoganoid polypeptide-encoding mRNA. In one embodiment, the nucleic acid is at least 15 nucleotides in length. In another embodiment, the nucleic acid is selected from the group consisting of an RNAi molecule, an antisense RNA molecule, a ribozyme and a DNAzyme.

This invention also provides a host-vector system comprising a cell having therein a replicable vector comprising a nucleic acid encoding a mahoganoid polypeptide, or a portion thereof having ubiquitin ligase activity. In one embodiment, the cell is a eukaryotic cell. In further embodiment, the cell is a mammalian cell. In another embodiment, the cell is a bacterial cell.

This invention also provides an antibody which specifically binds to an isolated mahoganoid polypeptide, or a portion thereof having ubiquitin ligase activity. In one embodiment, the antibody is labeled with a detectable moiety, such as a radioisotope, an enzyme, a fluorogenic material, a chemiluminescent material or an electrochemical material.

This invention also provides a composition of matter comprising an isolated nucleic acid encoding a mahoganoid polypeptide, or a portion thereof having ubiquitin ligase activity and a pharmaceutically acceptable carrier.

This invention also provides a composition of matter comprising an isolated mahoganoid polypeptide, or a portion thereof having ubiquitin ligase activity and a pharmaceutically acceptable carrier.

This invention also provides a composition of matter comprising an isolated nucleic acid that specifically hybridizes to mahoganoid polypeptide-encoding mRNA and a pharmaceutically acceptable carrier.

This invention also provides a method for decreasing the amount of mahoganoid polypeptide in a cell comprising contacting the cell with an agent that specifically inhibits mahoganoid polypeptide expression in the cell, thereby decreasing the amount of mahoganoid polypeptide in the cell. In one embodiment, the cell is a mammalian cell. In a further embodiment, the cell is a mouse cell. In further embodiment, the cell is a human cell. In another embodiment, the cell is a neuron. In a further embodiment, the agent is the instant anti-sense nucleic acid.

This invention also provides a method for decreasing the amount of mahoganoid polypeptide in a subject's cells comprising administering to the subject an agent that specifically inhibits mahoganoid polypeptide expression in a cell, thereby decreasing the amount of mahoganoid polypeptide in the subject's cells. In one embodiment, the subject is a mammal. In a further embodiment, the subject is a mouse. In a further embodiment, the subject is a human. In a further embodiment, the agent is the instant anti-sense nucleic acid.

This invention also provides a method for treating an overweight subject comprising administering to the subject a therapeutically effective amount of an agent that specifically inhibits mahoganoid polypeptide expression in a cell, thereby treating the subject. In a further embodiment, the agent is the instant anti-sense nucleic acid.

This invention also provides a method for inhibiting the onset of weight gain in a subject comprising administering to the subject a prophylactically effective amount of an agent that specifically inhibits mahoganoid polypeptide expression in a cell, thereby inhibiting the onset of weight gain in the subject. In a further embodiment, the agent is the instant anti-sense nucleic acid.

This invention also provides an article of manufacture comprising a packaging material having therein an agent that specifically inhibits mahoganoid polypeptide expression in a cell, and a label indicating a use for the agent in treating an overweight subject and/or inhibiting the onset of weight gain in a subject.

This invention also provides a method for determining whether an agent decreases mahoganoid polypeptide expression in a cell, which method comprises the steps of
   (a) contacting the cell with the agent under suitable conditions;
   (b) determining the amount of mahoganoid polypeptide expression in the cell after a suitable period of time; and
   (c) comparing the amount of mahoganoid polypeptide expression determined in step (b) with the amount of mahoganoid polypeptide expression in a cell in the absence of the agent, whereby a lower amount of mahoganoid polypeptide expression in the cell contacted with the agent, relative to the amount of expression in the absence of the agent, indicates that the agent decreases mahoganoid polypeptide expression in the cell.

This invention also provides a method for determining whether an agent inhibits the ubiquitin ligase activity of mahoganoid polypeptide, which method comprises the steps of
   (a) contacting mahoganoid polypeptide and ubiquitin with the agent under conditions which would permit mahoganoid polypeptide ubiquitin ligase activity in the absence of the agent;
   (b) determining the amount of ubiquitin ligated after a suitable period of time; and
   (c) comparing the amount of ligated ubiquitin determined in step (b) with the amount of ligated ubiquitin in the absence of the agent, whereby a lower amount of ligated ubiquitin in the presence of the agent, relative to the amount of ligated ubiquitin in the absence of the agent, indicates that the agent inhibits the ubiquitin ligase activity of mahoganoid polypeptide.

In one embodiment, a suitable period of time is within 4 days. In a second embodiment, a suitable period of time is within 2 days. In another embodiment, a suitable period of time is within 1 day. In further embodiments, a suitable period of time is within 12 hours or 6 hours.

This invention also provides a method for increasing the amount of mahoganoid polypeptide in a cell comprising contacting the cell with an agent that specifically increases mahoganoid polypeptide expression in the cell, thereby increasing the amount of mahoganoid polypeptide in the cell. In one embodiment, the cell is a mammalian cell. In a further embodiment, the cell is a mouse cell. In further embodiment, the cell is a human cell. In another embodiment, the cell is a neuron. In a further embodiment, the agent is the instant polypeptide or nucleic acid encoding same.

This invention also provides a method for increasing the amount of mahoganoid polypeptide in a subject comprising administering to the subject an agent that specifically increases mahoganoid polypeptide expression in a cell, thereby increasing the amount of mahoganoid polypeptide in the subject. In one embodiment, the subject is a mammal. In a further embodiment, the subject is a mouse. In further embodiment, the subject is a human. In a further embodiment, the agent is the instant polypeptide or nucleic acid encoding same.

This invention also provides a method for treating an underweight subject comprising administering to the subject a therapeutically effective amount of an agent that specifically increases mahoganoid polypeptide expression in a cell, thereby treating the subject. In a further embodiment, the agent is the instant polypeptide or nucleic acid encoding same.

This invention also provides a method for inhibiting the onset of weight loss in a subject comprising administering to the subject a prophylactically effective amount of an agent that specifically increases mahoganoid polypeptide expression in a cell, thereby inhibiting the onset of weight loss in the subject. In a further embodiment, the agent is the instant polypeptide or nucleic acid encoding same.

This invention also provides an article of manufacture comprising a packaging material having therein an agent that specifically increases mahoganoid polypeptide expression in a cell, and a label indicating a use for the agent in treating an underweight subject and/or inhibiting the onset of weight loss in a subject.

This invention also provides a method for determining whether an agent increases mahoganoid polypeptide expression in a cell, which method comprises the steps of
   (a) contacting the cell with the agent under suitable conditions;
   (b) determining the amount of mahoganoid polypeptide expression in the cell after a suitable period of time; and
   (c) comparing the amount of mahoganoid polypeptide expression determined in step (b) with the amount of mahoganoid polypeptide expression in a cell in the absence of the agent, whereby a higher amount of mahoganoid polypeptide expression in the cell contacted with the agent, relative to the amount of expression in the absence of the agent, indicates that the agent increases the amount of mahoganoid polypeptide expression in the cell.

This invention also provides a method for determining whether an agent increases the ubiquitin ligase activity of mahoganoid polypeptide, which method comprises the steps of
   (a) contacting mahoganoid polypeptide and ubiquitin with the agent under conditions which would permit mahoganoid polypeptide ubiquitin ligase activity in the absence of the agent;
   (b) determining the amount of ligated ubiquitin after a suitable period of time; and
   (c) comparing the amount of ligated ubiquitin determined in step (b) with the amount of ligated ubiquitin in the absence of the agent, whereby a higher amount of ligated ubiquitin in the presence of the agent, relative to the amount of ligated ubiquitin in the absence of the agent, indicates that the agent increases the ubiquitin ligase activity of mahoganoid polypeptide.

This invention also provides a method for treating a subject suffering from spongiform degeneration (40) comprising administering to the subject a therapeutically effective amount of an agent that specifically increases mahoganoid polypeptide expression in a cell, thereby treating the subject.

Finally, this invention provides an article of manufacture comprising a packaging material having therein an agent that specifically increases mahoganoid polypeptide expression in a cell, and a label indicating a use for the agent in treating a subject suffering from spongiform degeneration.

Determining a therapeutically or prophylactically effective amount of the instant polypeptide and nucleic acids can be done based on animal data using routine computational methods. In one embodiment, the therapeutically or prophylactically effective amount contains between about 0.1 mg and about 1 g of nucleic acid or polypeptide, as applicable. In another embodiment, the effective amount contains between about 1 mg and about 100 mg of nucleic acid or polypeptide, as applicable. In a further embodiment, the effective amount contains between about 10 mg and about 50 mg of the nucleic acid or polypeptide, as applicable.

This invention will be better understood from the Experimental Details that follow. However, one skilled in the art will readily appreciate that the specific methods and results discussed are merely illustrative of the invention as described more fully in the claims which follow thereafter.

EXPERIMENTAL DETAILS

Synopsis

Here we report the positional cloning of the mouse mahoganoid through a combination of genetic mapping and bioinformatics approaches.

Methods

Figure 2:
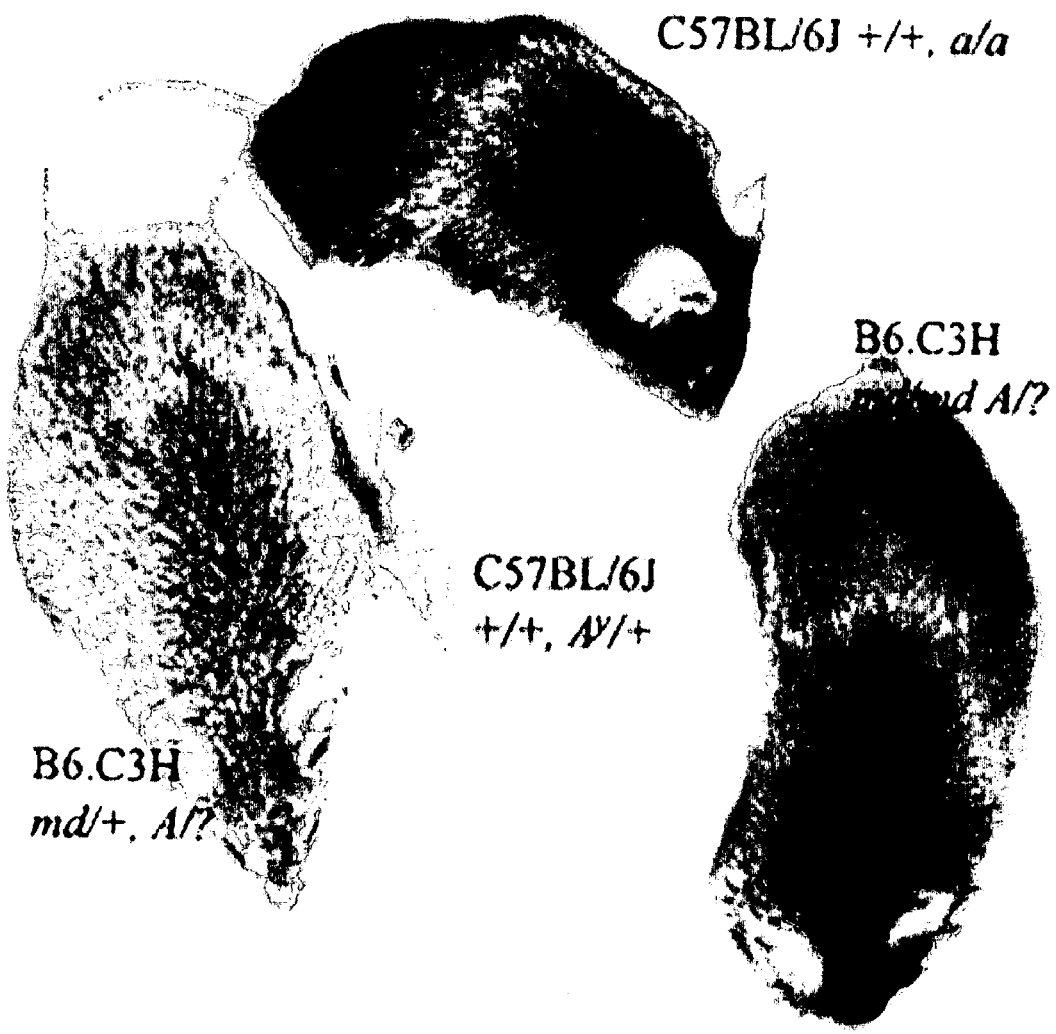

Animals. N7F14 B6.C3H-md-A (md/md and md/+) mice were obtained from the Jackson Laboratory (Bar Harbor, Me.). The coat color effect of the mutation is easiest to detect on an agouti (A) coat (FIG. 2); hence these animals have been selected and bred for phenotypes at 2 loci on different chromosomes (md and A). Progeny for genetic mapping of the region around md were generated by mating md/md A/?×md/+ A/? animals of this congenic strain. The fact that this line was maintained by coat color selection offered the opportunity to map, and reduce by meiotic recombination, the C3H genetic interval containing the md locus. Mice were housed in a barrier facility under pathogen-free conditions with a 12 hour light/dark cycle. Mice were weaned at 21 days and were then given ad libitum access to 9% kcal fat Picolab Rodent Chow 20 (Purina Mills, Richmond, Ind.) or to 45% kcal fat D12451 (Research Diets, Inc., New Brunswick, N.J.). Mice were fasted for 2 hours prior to sacrifice by $CO_2$ asphyxiation at 105-120 days of age. Weight and nasoanal body length were measured. The kidneys were removed and immediately frozen at −80° C. for subsequent isolation of genomic DNA. Other mice used were: B6.V-

Lep$^{ob}$ (N30), B6.Cg-A$^y$ (N66), C57BL/6J (F217), C3H/HeJ (F243), and C3H/HeJ-md$^{2J}$ (N2). All were obtained from the Jackson Laboratory.

Microsatellite Genotyping. Genomic DNA was made from tail tips clipped at weaning using QIAamp Tissue Kit (Qiagen mc, Valencia, Calif.). Mice were genotyped for Whitehead Institute microsatellites in the region of md by polymerase chain reaction (PCR) amplification. D16Mit182, D16Mit107, D16Mit154, D16Mit130, D16Mit129, D16Mit54, D16Mit159, D16Mit122, and D16Mit81 were scored using primers obtained from Research Genetics (Huntsville, Ala.). PCR conditions consisted of 40 cycles of denaturation at 94° C. for 30 sec, annealing at 55° C. for 30 sec, and extension at 72° C. for 45 sec. PCR fragments were resolved on 6% denaturing polyacrylamide gels.

Genetic and Physical Mapping. One hundred forty-nine progeny of an N7F14 B6.C3H-md/md A/! x N7F14 B6.C3H-md/+ A/! cross were used for genetic mapping of mahoganoid. Homozygosity for md was scored by observation of coat color (FIG. 2) Homozygosity for md results in a darkening of the agouti coat color (umbrous); md/+ mice have an agouti coat color. Initially, the congenic C3H interval containing md was defined by scoring congenic B6.C3H-md/md A/? mice with microsatellite markers on proximal chromosome 16 for B6 and C3H alleles. Next, all 149 progeny were scored for D16Mit182, D16Mit107, D16Mit154, D16Mit130, D16Mit129, D16Mit54, D16Mit159, D16Mit122, and D16Mit81to identify recombinant md/md animals with B6/C3H heterozygous genotypes and md/+ animals with C3H/C3H homozygous genotypes. Once the minimal genetic interval was defined, all expressed sequence tags (ESTs) within the interval were obtained from the Whitehead radiation hybrid (RH) map. Mouse and corresponding human genomic clones were identified through nBlast of ESTs and mouse microsatellite markers to online sources. Mouse genomic clones were used to search these databases to construct a complete 2.5 Mb contig of mouse BAC clones spanning the minimal interval containing md. All transcripts in the interval were identified using Celera and NCBI databases.

Sequence Analysis of Positional Candidate Genes. To screen for mutations in the coding sequences of the transcripts and predicted genes mapping to the minimal contig, each of the exons was amplified from genomic DNA by PCR followed by amplicon purification by QIAquick Gel Extraction Kit (Qiagen Inc, Valencia, Calif.) and bidirectional fluorescent dideoxy termination sequencing (20). This process was prioritized so that the known transcripts were screened before the predicted genes. Sequences from C3H/HeJ +/+ and C3H/HeJ md$^{2J}$/md$^{2J}$ [coisogenic on C3H/HeJ] were compared using Sequencher software 4.0.5 (Gene Codes Corp, Ann Arbor, Mich.).

Southern Blot Analysis. Genomic DNA of affected md, md$^{2J}$, md$^{4J}$, md$^5$, and md$^{6J}$ obtained from the Jackson Laboratory was analyzed by Southern blot analysis (21) using restriction enzymes Pst I, EcoR I, Hind III, Sau3AI, Msp I, and Bgl II (Roche, Ridgefield, Conn.). Restriction fragments were separated by electrophoiesis on 0.7% agarose gels, transferred by capillary action to a nylon membrane (Schleicher & Schuell Inc., Keene, N.H.), prehybridized (Ultrahyb; Ambion Inc., Woodward, Tex.), and hybridized using a random-primed $^{32}$P-labeled C3H/HeJ genomic PCR-amplified fragment prepared using the following primers: Probe 1, F: 5'-GATGGGGCTTGAGTCCT-TAGA-3' (SEQ ID NO: 14), R: 5'-CCTCAGCCCAG-CACTTTCTCT-3' (SEQ ID NO: 15) flanking exon 12 of Riken full-length cDNA AK011747 (shown by mutation analysis to contain the md gene, see below); and Probe 2, F: 5'-GGCAGGTGGGAACAGATGAGT-3' (SEQ ID NO: 16), R: 5'-CCGTCCGAGATGCCTGAGTAG-3' (SEQ ID NO: 17), spanning the intronic region between exon 11 and exon 12. Two cDNA probes (Probes 3 and 4) spanning, respectively, exons 2-9 and exons 3-13 of AK011747, were prepared from pooled C57BL/6J cDNA obtained from liver, kidneys, lungs, spleen, brain, adipose, pancreas, and heart cDNA using the following primers: Probe 3, F: 5'-TTGA-CACTCCCCATCCTGAAG-3' (SEQ ID NO: 18), R: 5'-TC-CTGGTTGTTCTTGTTCTCG-3' (SEQ ID NO: 19), and Probe 4, F: 5'-CCAGTTTCCCTATGTCACCCC-3' (SEQ ID NO: 20), R: 5'-ATGGATGGGGAATGATGGAGA-3' (SEQ ID NO: 21). The blots were washed 36. Weissman, A. M. (2001). Themes and variations on ubiquitylation. *Nat Rev Mol Cell Bid* 2:169-178.

37. Layfield, R., Alban, A., Mayer, J. R. and Lowe, J. (2001). The ubiquitin protein catabolic disorders. *Neuropathology and Applied Neurobiology* 2.7: 171-179.

38. Kwon, Y. T., Xia, Z., Davydov, I. V., Lecker, S. H., and Varshavsky, A. 2001. Construction and analysis of mouse strains lacking the ubiquitin ligase UBRi (E3α) of the N-end rule pathway. *Mol. Cell Biol.* 21:8007-8021.

39. Francke, S., Manraj, M., Lacquemant, C., Lecoeur, C., Lepretre, F., Passa, P., Hebe, A., Corset, L., Yan, S. L., Lahmidi, S., et al. (2001). A genome-wide scan for coronary heart disease suggests in Indo-Mauritians a susceptibility locus on chromosome 16p13 and replicates linkage with the metabolic syndrome on 3q27. *Hum Mol Genet* 10:27512765.

40. He, L., Lu, X.-Y., Jolly, A. F., Eldridge, A. G., Watson, S. J., Jackson, P. K., Barsh, G. S. and Gunn, T. M. (2003). Spongiform Degeneration in mahoganoid Mutant Mice. *Science* 299:710-712. in 1X SSC/0.1% SDS twice for 10 minutes at room temperature and twice for 30 minutes at 64° C. and exposed to X-ray film (RX-B; Denville, Metuchen, N.J.) at -80° C. for 48 hrs.

Northern Blot Analysis. Northern blots of liver, heart, kidney, lung, skin, skeletal muscle, adipose, and brain tissue were performed using standard techniques (21). Total RNA was extracted using a commercial kit (Trizol; Invitrogen, Carlsbad, Calif.) and size fractionated on a 1% agarose formaldehyde gel. Blot handling was as for Southern blots. Only probe 4 was used for Northern hybridizations.

Real time RT-PCR. RNA was extracted from flash-frozen, freshly dissected whole organs using a commercial kit (Trizol; Invitrogen, Carlsbad, Calif.) and purified using RNeasy Mini kits (Qiagen Inc., Valencia, Calif.). cDNA was then made using SuperScript First-Strand Synthesis System for RT-PCR (Invitrogen, Carlsbad, Calif.) with 50 ng of random hexainers for each mg of total RNA. A negative control for cDNA was made in an identical manner without adding the SuperScript II RT to each tube. cDNA was diluted five-fold prior to use. A LightCycler (Roche, Mannheim, Germany) was used to quantify expression levels with 20 µl reactions consisting of 2 µl diluted cDNA, 16 µl FastStart DNA Master SYBR Green I mix (Roche, Mannheim, Germany) and 2 µl of primers (F: 5'-TGTCTCCCATCTCCT-TCAGCC-3' (SEQ ID NO: 22); R: 5'-CTGTGTCTTGC-CCTTCTGTAG-3') (SEQ ID NO: 23) spanning exon 11-12 of Riken cDNA AK011747. Each sample was run in triplicate with one negative control. β-actin (F: 5'-ATCGCT-GCGCTGGTCGTC-3' (SEQ ID NO: 24); R: 5'-GCTCTGGGCCTCGTCACC-3' (SEQ ID NO: 25)) was used to normalize expression levels. Only one product was seen on the melting curves, so fluorescent acquisition was set at the extension stage. Relative expression levels were found by comparing expression levels in each organ to the level found in +/+ C57BL/6J mice in the same organ (22). PCR fragments were resolved on 2% agarose gel.

Generating Restriction Maps of md Genomic Sequence. Ensembl gene ENSMUSG00000022517, containing the complete genomic sequence of md, was identified through nBlast of transcript AK011747 into genomic DNA database Ensembl (Ensembl, Cambridge, United Kingdom). The genomic sequence obtained was used as a control template in creating the restriction map for the md. Sequencher software 4.0.5 (Gene Codes Corp, Ann Arbor, Mich.) was used on both the normal and inserted retroviral sequences to determine the restriction sites and fragment sizes for specific restriction enzymes.

Neuropathology. Fifteen week old C3H.B6 md/md A/? and C57BL/6J +/+ male and female mice were sacrificed by CO2 asphyxiation, and the whole brain fixed overnight in 3.7% paraformaldehyde in phosphate buffered saline. One year old C3H.B6 md/md A/? male and female mice were also examined. Serial paraffin sections including cortex, hippocampus, pons, thalamus, cerebellum, brain stem, midbrain and hypothalamus were cut and stained with hematoxylin and eosin (23). These sections were examined by light microscopy by Dr. James Goldman (Department of Pathology, Columbia University).

Body Weight and Length. To assess the effects of md on energy homeostasis, at sacrifice at 105-120 days, body weight and nasoanal length were measured in male and female md/+ and md/md animals that had ingested 9% or 45% kcal fat diets since weaning at about 21 days of age.

Results

Figure 3:
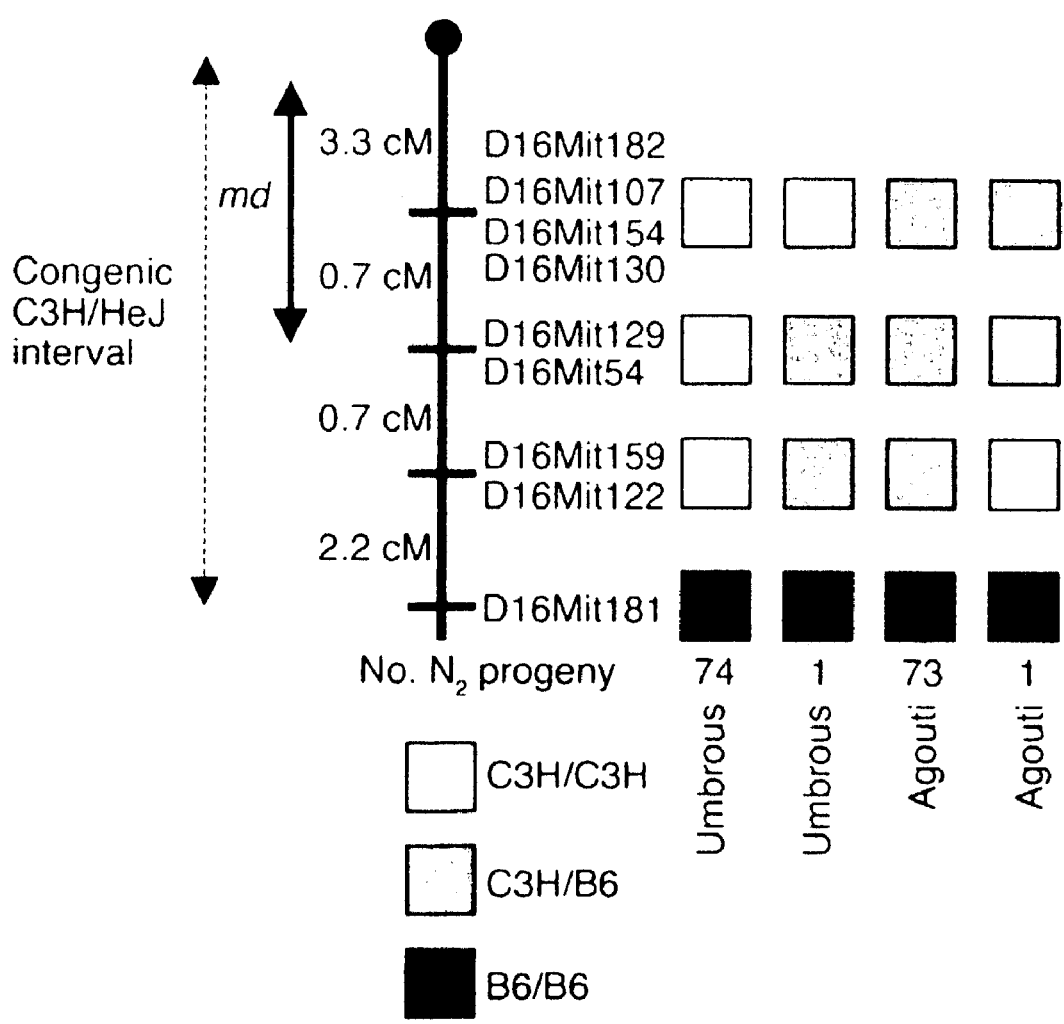

By genotyping congenic B6.C3H-md/md A/? mice for microsatellite genetic markers polymorphic between C57BL/6J and C3H/HeJ, the maximal congenic C3H/HeJ interval was determined to extend approximately 6.9 cM from the centromere to D16Mit181 (FIG. 3). Genetic mapping of 149 progeny of a B6.C3H-md/+ A/?×B6.C3H-md/md A/? intercross, in which genotype for md was assigned by coat color, identified a double recombination event in the C3H congenic interval between markers D16Mit122/D16Mit159 distally and markers D16Mit54/D16Mit129 proximally. Similarly, there was a single md/md mouse with a recombination between D16Mit54/D16Mit129 and D16Mit130/D16Mit154/D16Mit107/D16Mit182, narrowing the interval containing md to a region of approximately 4.0 cM proximal to D16Mit54/D16Mit129 (FIG. 3).

Figures 4A, 4B, 4C:
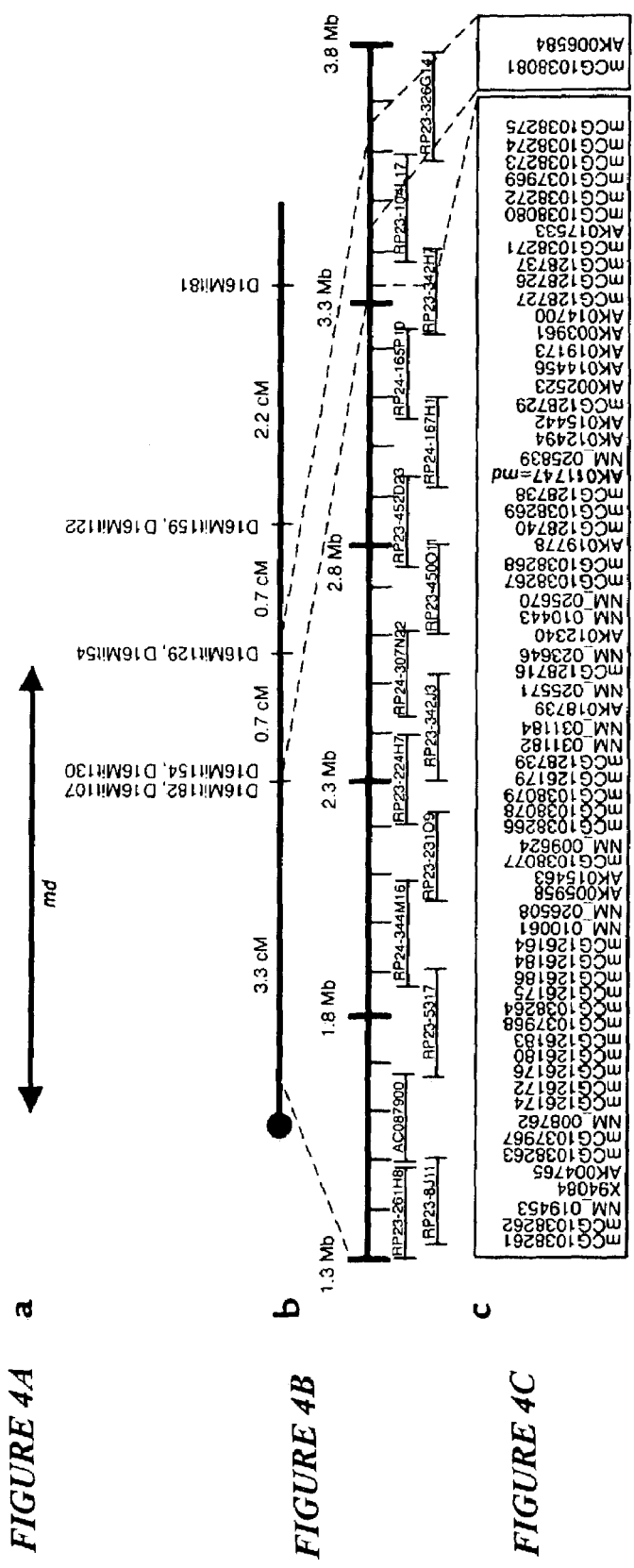

Using sequence databases at NCBI, Celera, Ensembl, Jackson Laboratory, and UCSC (see Methods for URL information), all mouse genomic clones in the 2.5 Mb interval containing md proximal to D16Mit129 and D16Mit54 were identified (FIG. 4). Twenty-nine transcripts and 39 computationally-predicted genes (24) were identified. Using nBlast, transcripts were compared against the Ensembl mouse cDNA database to obtain genomic sequences with exon predictions. These genes were then systematically analyzed as indicated below. The coding regions of 27 of the 29 known transcripts, excluding X94084 and AK004765, were systematically sequenced in $md^{2J}$ and coisogenic C3H/HeJ +/+ animals. By virtue of the disruptions described below in $md^{2J}$ and other members of the mahoganoid allelic series, Riken cDNA AK011747 was implicated as the mahoganoid transcript.

Figure 5A:
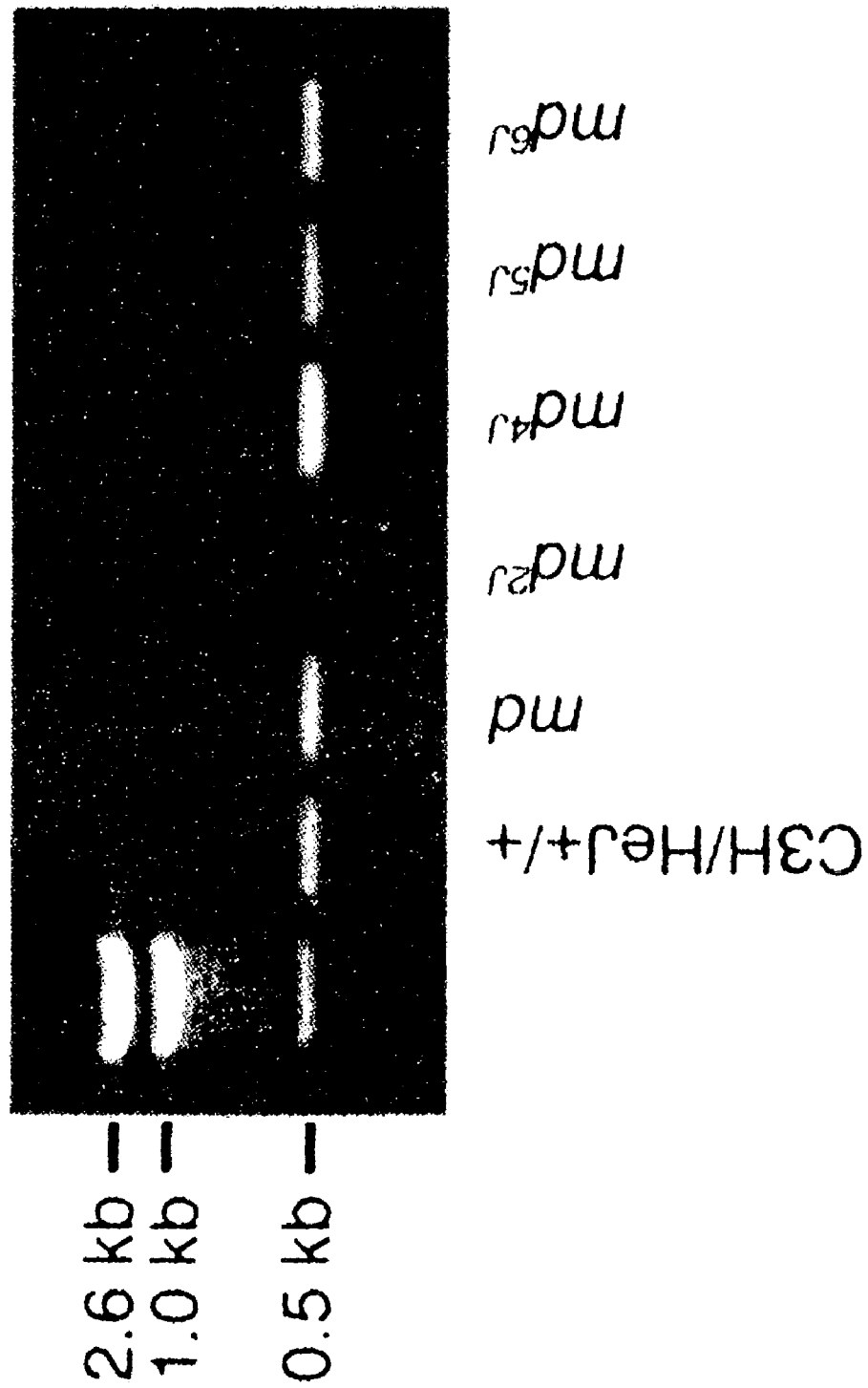
Figure 5B:
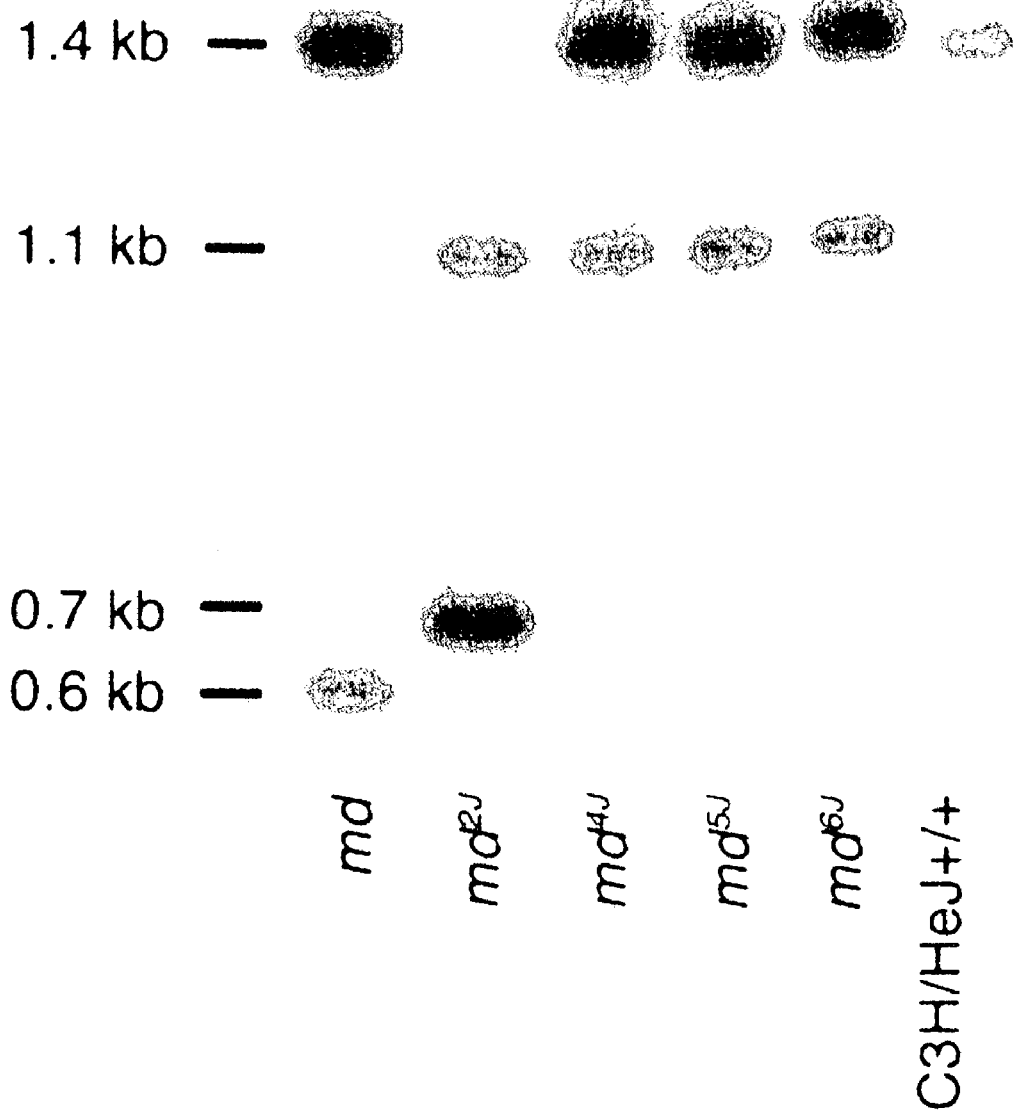
Figure 6:
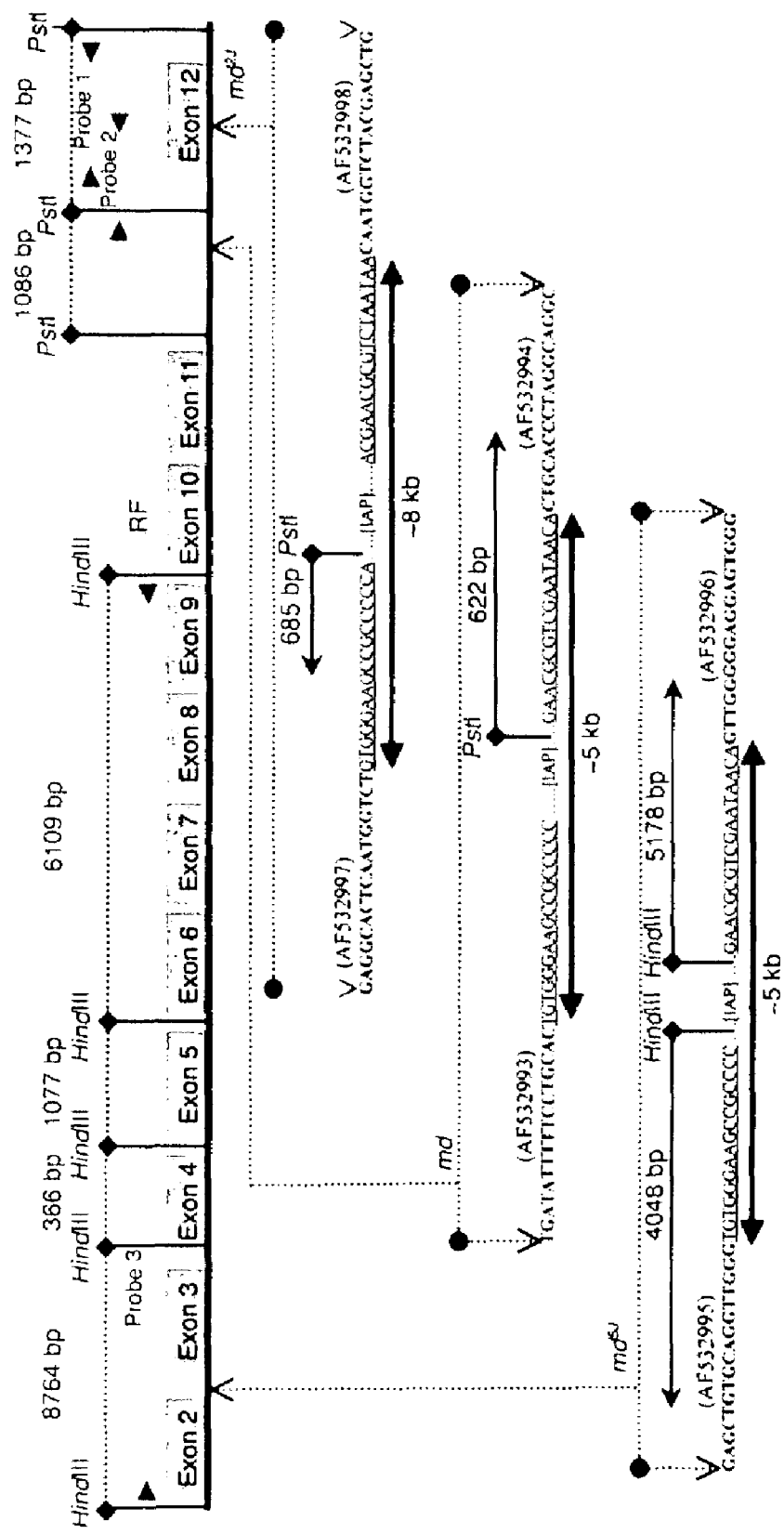

$md^{2J}$, an 8 kb retroviral insertion within exon 12. Each of the predicted coding sequences of ESTs, known genes, and computationally predicted genes in the minimum physical interval for mahoganoid were amplified from genomic DNA of an $md^{2J}/md^{2J}$ mouse and a co-isogenic non mutant animal using intronic primers flanking the known or predicted exons in the interval. For the Riken cDNA clone AK011747, all exons except exon 12 were amplified from both the $md^{2J}/md^{2J}$ and C3H/HeJ +/+. For exon 12, the normal 589 bp C3H/HeJ allele could be amplified in the +/+ as well as all of the md alleles except $md^{2J}$ (FIG. 5A). PCR amplification and subsequent bidirectional sequencing of predicted coding exons 2-16 from homozygous affected md, $md^{2J}$, $md^{4J}$, $md^{5J}$ and $md^{6J}$ mice demonstrated normal genomic sequence. Southern blot analysis of $md^{2J}/md^{2J}$ animals restricted with Pst I, using probe 2, that contained part of exon 12 and its 5' intronic region, showed a novel 0.7 kb fragment in the $md^{2J}/md^{2J}$ animal compared with a 1.4 kb fragment corresponding to exon 12 in the C3H/HeJ co-isogenic +/+ control and in mahoganoid alleles (md, $md^{4J}$, $md^{5J}$, $md^{6J}$) (FIG. 5B). The region of probe 2 containing part of exon 12 and its 5' intronic region was then amplified and sequenced from genomic DNA and demonstrated an ~8 kb insertion in exon 12 of $md^{2J}$ (data not shown). The fragment was shown by sequence analysis to be a retroviral insertion (GenBank: AF532997, AF532998) (SEQ ID NOs: 5 and 6) containing a Pst I restriction site (FIG. 6)

Figure 5C:

$md^{5J}$, a 5 kb retroviral insertion in the intron 3' of exon 2. Southern blot analysis of $md^{5J}$ DNA restricted with HindIII (but not PstI, EcoRI, BglII, or Sau3AI), and probed with a cDNA corresponding to exons 2-9, demonstrated a different restriction pattern than the C3H/HeJ co-isogenic +/+ control and the other md alleles (FIG. 5C). The $md^{5J}$ DNA showed loss of an 8.8 kb fragment corresponding to the region of exons 2-4 and introduction of new 5.2 kb and 4.0 kb fragments. Similar results were obtained with a cDNA probe spanning exons 3-5 (data not shown). PCR amplification of genomic $md^{5J}$ DNA corresponding to the intronic region between exon 2 and exon 3 demonstrated a fragment ~5 kb larger than the C3H/HeJ co-isogenic +/+ control (data not shown). Sequence analysis showed that $md^{5J}$ is a retroviral insertion (GenBank: AF532995, AF532996) (SEQ ID NOs: 3 and 4) of ~5 kb in the intronic region 3' of exon 2 (FIG. 6). md, a 5 kb retroviral insertion in the intron between exons 11-12. Southern blot analysis of a PstI digest of md using probe 2 demonstrated a missing fragment of 1.1 kb and the presence of a new fragment of 0.6 kb corresponding to the intronic region 5' of exon 12 (FIG. 5B). PCR amplification in md genomic DNA of the intron between exons 11 and 12 demonstrated a fragment ~5 kb larger than the C3H/HeJ co-isogenic +/+, suggesting that the md mutation is due to an insertion in this intron (data not shown). Sequence analysis of the PCR-amplified genomic DNA between exons 11 and 12 showed an inserted retroviral sequence (GenBank: AF532993, AF532994) (SEQ ID NOs: 1 and 2) within the intron (FIG. 6)

The insertions are intracisternal type A particle elements. Comparison of the 5' and 3' regions of the insertions detected in md, $md^{2J}$, and $md^{5J}$ with GenBank entries revealed that the insertion is a mouse retrovirus-like repetitive intracisternal type A particle (IAP) element matching GenBank X04120. The IAP seen in the mahoganoid mutations reported here is similar to the element reported in mahogany ($Atrn^{mg}$ and $Atrn^{mg-L}$) (12). The integrated IAP elements associated with the md mutations were flanked in all instances with canonical long terminal repeat (LTR) sequences that are frequently observed in contiguous to retroviral IAP insertions (25).

Expression of mahoganoid alleles. Northern blot analysis, using probe 5 that spans exons 3-13 containing the RING (really interesting new gene) finger domain in exon 10, demonstrated a 3.9 kb mahoganoid transcript expressed in kidney, brain, heart, spleen, lung, skin, skeletal muscle, and adipose tissue in B6.V-Lep$^{op}$, B6.Cg-A$^y$, and C57BL/6J +/+ mice (FIG. 7A). An additional transcript of 5.2 kb was also seen in the kidney, brain, and liver; and a transcript of 1.9 kb in the kidney of C57BL/6J +/+, B6.V-Lep$^{ob}$, and B6.Cg-A$^y$ mice (FIG. 7A). Both were at lower levels of expression than the 3.9 kb transcript. Expression levels of the 3.9 kb and 5.2 kb transcripts were 10- to 20-fold lower in the md/md and md$^{2J}$/md$^{2J}$ animals. Additionally, several aberrantly sized transcripts of 5.9, 5.5, 4.1, and 2.2 kb were observed in md/md animals, and 12.0 kb and 3.6 kb transcripts in md$^{2J}$/md$^{2J}$ (FIG. 7B). The aberrantly sized transcripts were not sequenced.

Using NCBI and Ensembl databases, KIAA0544 was identified as the human homolog of md. Like md, KIAA0544 is predicted to have 17 exons with a RING finger domain located in exon 10. NCBI Aceview analysis (http://www.ncbi.nih.gov/IEB/Research/Acembly/av.cgi?db=28&1=Hs16_10709_29_1_t16_Hs16_10709_29_2_5347.a) of KIAA0544 showed that the human homolog of md is defined by 139 sequences from 129 cDNA clones and produces, by alternative splicing, 6 mRNAs of variant a, 4.1 kb; variant b, 3.9 kb; variant c, 5.2 kb; variant d, 1.9 kb; variant e, 2.4 kb; and variant f, 2.2 kb. Using probe 4, which spans exons 3-13, only md transcripts of 3.9 kb, 5.2 kb, and 1.9 kb were detected in Northern blots. These transcripts are similar in size to human transcripts b, c, and d. The human 5.2 kb transcript is alternatively spliced to incorporate an additional 66-bp exon between exons 11 and 12 of the 3.9 kb transcript as well as to use an alternative splice site for the final exon. Further blast analysis of md transcript AK011747 in the TIGR Mouse (*Mus musculus*) gene index (MGI) (http://www.tigr.org/tigr-scripts/tgi/tc_report.pl?species=mouse&tc=TC457132) identified mouse EST TC457132 that corresponds to the human 5.2 kb transcript. An expression profile of KIAA0544 in 14 different tissues (heart, brain, placenta, lung, liver, skeletal muscle, kidney, pancreas, spleen, thymus, prostate, testis, ovary, and small intestine) generated by RT-PCR, indicates that the human homolog has a similar expression pattern as mahoganoid in the mouse (26).

By quantitative RT-PCR using primers spanning exons 11-12, mahoganoid expression levels relative to actin were found to be similar in the brain and kidney among genetically obese Lep$^{ob}$/Lep$^{ob}$ and A$^y$/+ mice and C57BL/6J +/+ controls (Table 1).

TABLE 1

Expression levels of mahoganoid by quantitative RT-PCR
Relative Expression Level

|  | Kidneys | Brain |
|---|---|---|
| B6.V-Lep$^{ob}$ | 0.760 | 1.15 |
| B6.Cg-A$^y$ | 0.993 | 1.10 |
| C57BL/6J | 1 | 1 |
| B6.C3H-md-A | 0.0950 | 0.0501 |
| C3H/HeJ md$^{2J}$ | 0.0598 | 0.0144 |

However, mahoganoid expression in the brain of md/md and md$^{2J}$/md$^{2J}$ animals relative to actin was 5% and 1% of that of C57BL/6J +/+ controls (Table 1). The probe spanning exons 11-12 detects both the 3.9 kb and 5.2 kb transcripts. The quantitative RT-PCR results are consistent with the very low expression levels for these transcripts seen in the Northern blots of md and md$^{2J}$ RNA.

Mahoganoid does not suppress obesity related to a high fat diet. The dose-dependent effect of md in diminishing the obesity of A$^y$ mice is striking and clear (17). The effect of this mutation on body composition in circumstances in which the gene is not in epistatic apposition to an obesity mutation is reportedly more subtle (17). We examined this issue by estimating the mouse equivalent of the body mass index (BMI; weight in grams/nasoanal length in cm$^2$) (27) in progeny of the N$_7$F$_{14}$ B6.C3H-md-A md/md×md/+ intercross used for mapping and minimizing the C3H interval containing the md locus. The progeny were fed from the time of weaning at about 21 days with mouse chow containing either 9% or 45% Kcal fat. Body weight and nasoanal length were measured every 2 weeks and the animals were sacrificed at about 115 days when weight and nasoanal length were measured. BMI was used as a surrogate measure for adiposity (27). As expected, animals fed 45% Kcal as fat were heavier and had higher BMI than those fed 9% fat. However, no effect of md genotype was seen on body weight or BMI of animals fed either the 9% or 45% Kcal fat chow (Table 2).

TABLE 2

BMI* and Weight in progeny of the N$_7$F$_{14}$ B6.C3H-md-A md/md × md/+ intercross on 9% or 45% fat diet [mean value (SD)]

|  |  | BMI | Weight (gm) | Age (days) | N |
|---|---|---|---|---|---|
| 9% fat diet |  |  |  |  |  |
| Female | md/+ | .276 (.019) | 24.8 (2.7) | 108.1 (1.8) | 15 |
|  | md/md | .276 (.029) | 24.8 (3.0) | 107.9 (1.5) | 15 |
| Male | md/+ | .329 (.026) | 33.7 (1.9) | 109.2 (1.9) | 21 |
|  | md/md | .322 (.024) | 33.9 (2.1) | 107.7 (0.9) | 22 |
| 45% fat diet |  |  |  |  |  |
| Female | md/+ | .344 (.046) | 30.1 (5.6) | 114.1 (2.1) | 8 |
|  | md/md | .325 (.042) | 29.0 (5.2) | 113.8 (2.2) | 16 |
| Male | md/+ | .402 (.040) | 40.6 (4.0) | 114.6 (1.6) | 14 |
|  | md/md | .391 (.050) | 39.8 (4.9) | 114.0 (1.1) | 13 |

*Weight (grams)/naso-anal length (cm$^2$)

No significant diet-by-genotype interaction was seen for either BMI or body weight by ANOVA (Table 3).

TABLE 3

ANOVA for effects of md on body weight and BMI ANOVA for diet and genotype effects

| Effect | F | p-value | Dependent |
|---|---|---|---|
| Sex | 72.06 | <0.0001 | BMI |
|  | 223.30 | <0.0001 | Weight |
| Diet (9% or 45% fat) | 10.34 | 0.002 | BMI |
|  | 0.34 | 0.56 | Weight |
| Genotype at md | 0.94 | 0.34 | BMI |
|  | 0.05 | 0.83 | Weight |
| Sex/Diet (interaction) | 0.95 | 0.33 | BMI |
|  | 1.73 | 0.19 | Weight |
| Sex/Genotype (interaction) | 0.12 | 0.73 | BMI |
|  | 0.53 | 0.47 | Weight |
| Diet/Genotype (interaction) | 0.96 | 0.33 | BMI |
|  | 1.18 | 0.28 | Weight |
| Sex/Diet/Genotype (interaction) | 0.15 | 0.70 | BMI |
|  | 0.07 | 0.79 | Weight |

It is important to note that we looked only at md/+ and md/md animals in this analysis because these were the only genotypes issuing from the md/+×md/md mapping cross.

Absence of a neurological phenotype in md/md mice. Md/md animals are neurologically normal at 15 weeks and at 1 year of age, without obvious tremor or movement disorder. Gross and microscopic examination of the midbrain, cerebellum, pons, hippocampus, hypothalamus, thalamus, cortex and brainstem demonstrated normal anatomy with no evidence of vacuolization or dysmyelination as is observed in the mahogany mouse (data not shown).

Mahoganoid encodes a 494 amino acid protein containing a C3HC4 RING domain from amino acids 240-278 (FIG.8). The human homologue, KIAA0544 maps to 16p13.3 and is 81% identical in amino acid sequence. The RING finger domain of KIAA0544 is 99% identical to mahoganoid C3HC4 RING domain. There are homologous genes in D. melanogaster and C. elegans with 43% and 37% identity of amino acids, respectively, that include the highly conserved C31-1C4 RING domains (FIG. 8)

Discussion

Coat color mutations in mice have provided unique insights into the molecular physiology of melanocortin-related control of coat color and energy homeostasis in mice and other mammals (28). Remarkably similar (sometimes identical) pathways/molecules are involved in these disparate phenotypes. G-protein-coupled melanocortin receptors (MC1R in skin, MC3R and MC4R in brain) mediate the effects of the physiologic ligand, α-MSH, and antagonists, ASP and AgRP (FIG. 1). Binding of a MSH to MC1R in the hair follicle, or to MC3R and MC4R in the hypothalamus, increases intracellular cAMP and increases the production of eumelanin in the hair follicle or decreases food intake by effects in the hypothalamus. Conversely, antagonism of MC1R by ASP in the hair follicle, or of MC4R by AgRP in the hypothalamus, produces increased pheomelanin in the hair follicle and increased food intake by effects in the hypothalamus. Constitutive overexpression of ASP in the $A^y$ mouse outside of the hair follicle best demonstrates the analogies between the two pathways since the yellow coat color of these mice is due to ASP antagonism of MC1R and the increased weight and adiposity is due to ASP antagonism of MC3R and MC4R in the hypothalamus (28). Other genes, such as mahogany and mahoganoid, modulate the activity of this pathway in skin and the brain (17). Here we present evidence that the mahoganoid allelic series is due to mutations in a RING finger protein whose function is unknown but that has a strong impact on the melanocortin signaling. Mutations in the mahoganoid allelic series (md, $md^{2J}$ and $md^{5J}$) are due to large retroviral insertions that disrupt the expression of md. Retroviral insertions have been shown to affect gene expression in other coat color mutations such as dilute (29), agouti (2), and mahogany (10). Tissue expression data indicate that md is ubiquitously expressed with highest expression in the brain and kidney. Expression of normal mahoganoid transcripts is greatly reduced in md/md and $md^{2J}/md^{2J}$ mice in all tissues examined by both Northern blot analysis and quantitative RT-PCR. The ability to identify md was greatly expedited by the availability of near complete human and mouse genomic sequence and annotation.

Mutations of md in mice act as suppressors of obesity and yellow coat color that are associated with constitutive overexpression of Asp in the $A^y$ mouse, but do not alter the yellow coat color phenotype of $Mc1r^e$ deficient mice (extension mutants) (17). Genetically, mutations in md are epistatic to $A^y$ and $Mc1r^e$ is epistatic to md, suggesting that mahoganoid is functionally distal to ASP and proximal to MC1R (FIG. 1). The epistatic relationship appears to be similar in the hair follicle and the hypothalamus since mahoganoid is able to suppress both the yellow coat color phenotype induced by constitutive ASP antagonism of MC1R as well as to suppress the obesity induced by ASP antagonism of MC3R and MC4R (17). Furthermore, these mutations of mahoganoid appear to be loss-of-function alleles because the phenotypes of the various alleles are all similar, and because mutations in the md and $md^{2J}$ alleles result in loss of normal gene expression in all tissues examined (FIG. 7). On the basis of similarities between the ASP/MC1R and AgRP/MC3R/MC4R pathways, we suggest that the normal mahoganoid allele acts through a similar mechanism in the hair follicle and hypothalamus, decreasing signaling through MC1R and MC3R/MC4R to produce increased pheomelanin production and increased body weight, respectively.

Both mg and md show epistatic effects on $A^y$ coat color and adiposity. Mahogany and mahoganoid have similar effects on coat color, but it is not yet clear if the mechanisms by which they confer their effects on body mass are similar. When expressed on an agouti (A/A or A/a) coat, mahogany mice have darker coat color than md (17). Mahogany fully suppresses $A^y$ obesity, while md rescues about 80% of the $A^y$ obesity phenotype (1). $Atrn^{mg}/Atrn^{mg}$ mice are leaner than +/+ mice of the same strain and have approximately 20% higher levels of energy expenditure by indirect calorimetry, possibly secondary to the muscle tremors attributable to the associated spongy degeneration in the central nervous system (14). The effects of mg and md on body weight in non-obese animals are much more subtle. Barsh reported that female A/A md/md animals fed standard lab chow were heavier than md/+ or +/+ animals at 12-40 weeks (17); we did not see this effect in our ~115 day old male and female animals fed 9% or 45% fat chow (Table 2). $Atrn^{mg}$ is due to deficiency of attractin, a transmembrane protein with binding specificity for ASP but not AgRP. Attractin is thought to act by localizing ASP to MC1R (10). $Atrn^{mg}$ specifically and fully suppresses obesity due to widespread overexpression of Asp in the $A^y$ mouse, possibly by virtue of loss of the ability to keep ASP in proximity to MC3R/MC4R in the hypothalamus and/or by virtue of the tremors caused by neurodegeneration (14). In comparison, mahoganoid mice (MD allele) have no obvious neurological, behavioral, gross or microscopic central nervous system anatomic phenotype. However, other alleles of mahoganoid (e.g. $md^{nc}$) have been shown to have neurologic and neuroanatomic phenotype (40). The quantity of Atrn expression in the various mg alleles parallels the effects of the mg alleles on pigmentation and neurodegeneration, with the $Atrn^{mg-3J}$ allele showing the lowest Atrn expression and having the most significant effects on coat color and neurodegeneration, while the $Atrn^{mg-L}$ allele conversely shows the highest Atrn expression and mildest phenotype (12).

The primary impact of mahoganoid on energy homeostasis is apparently via the melanocortin-signaling pathway(s) in the brain. This effect is clearest when amplified by overexpressing ASP in the brain (as in the $A^y$ animal). This situation is reminiscent of what is seen in the neuropeptide Y (Npy) knockout mouse, where despite a profound effect of the protein on food intake and energy metabolism, knockout of the gene does not have much effect on food intake or body composition of the knockout animal (30). However, $Npy^{-/-}$ substantially reduces the obesity of $Lep^{ob}/Lep^{op}$ mice (30). Additional studies of energy intake, energy expenditure and body composition will be required to assess the effects of md on energy homeostasis.

Mahoganoid is a ubiquitously expressed protein with a C3HC4 RING finger domain that is similar to the RING finger domain of the proto-oncogene c-Cbl. The RING finger, an evolutionarily conserved cysteine/histidine residue containing motif, Cys-X2-Cys-X9-39-Cys-X1-3-His-X2-3-Cys/His-X2-Cys-X4-48-Cys-X2-Cys (31), identified in more than 200 proteins, is a small zinc-binding domain often found in subunits of multiprotein complexes (32). The RING finger binds two zinc atoms in a unique "cross-brace" system. RING fingers are located close to amino or carboxyl termini of proteins and may be associated with other domains to form larger conserved motifs like the RING finger-B box-a-helical coiled-coil (RBCC) motif (31). The RING domain is a common structural element in a superfamily of E3 ubiquitin ligase complexes: e.g., SCF (Skp1-Cdc53/CUL1-F-box protein) family, APC (anaphase-promoting complex) family, c-Cbl and MDM2 proto-oncogene, and members of the IAP family of antiapoptotic proteins (33). Based on protein sequence homology to E3 RING domain ubiquitin ligases, mahoganoid may itself function as an E3 ubiquitin ligase (34).

Ubiquitylation involves conjugation of proteins with the highly conserved 76-amino acid protein, ubiquitin. The process targets proteins for degradation in the proteosome, vacuoles, or lysosomes, or regulates cellular processes through translational control, protein kinase activation, or transcriptional regulation (35, 36). The specificity of the ubiquitylation process is conferred by the E3 ubiquitin ligase, of which there are many (36). Ubiquitylation has been implicated in the regulation of myriad cellular processes including cell cycling, apoptosis, cellular differentiation, DNA repair, and stress responses. Inherited loss-of-function mutations in other E3 ubiquitin ligase genes have been implicated in juvenile Parkinson disease, Angelman syndrome, breast and ovarian cancer susceptibility (BRCA1), and von Hippel Lindau disease (37). Ubiquitylation proceeds through a three-step process, involving ubiquitin-activating (E1), ubiquitin-conjugating (E2), and ubiquitin-ligating (E3) enzymes. The E3 enzymes mediate the transfer of ubiquitin from the E2 to the substrate, and thereby confer substrate specificity (34).

Figure 9:
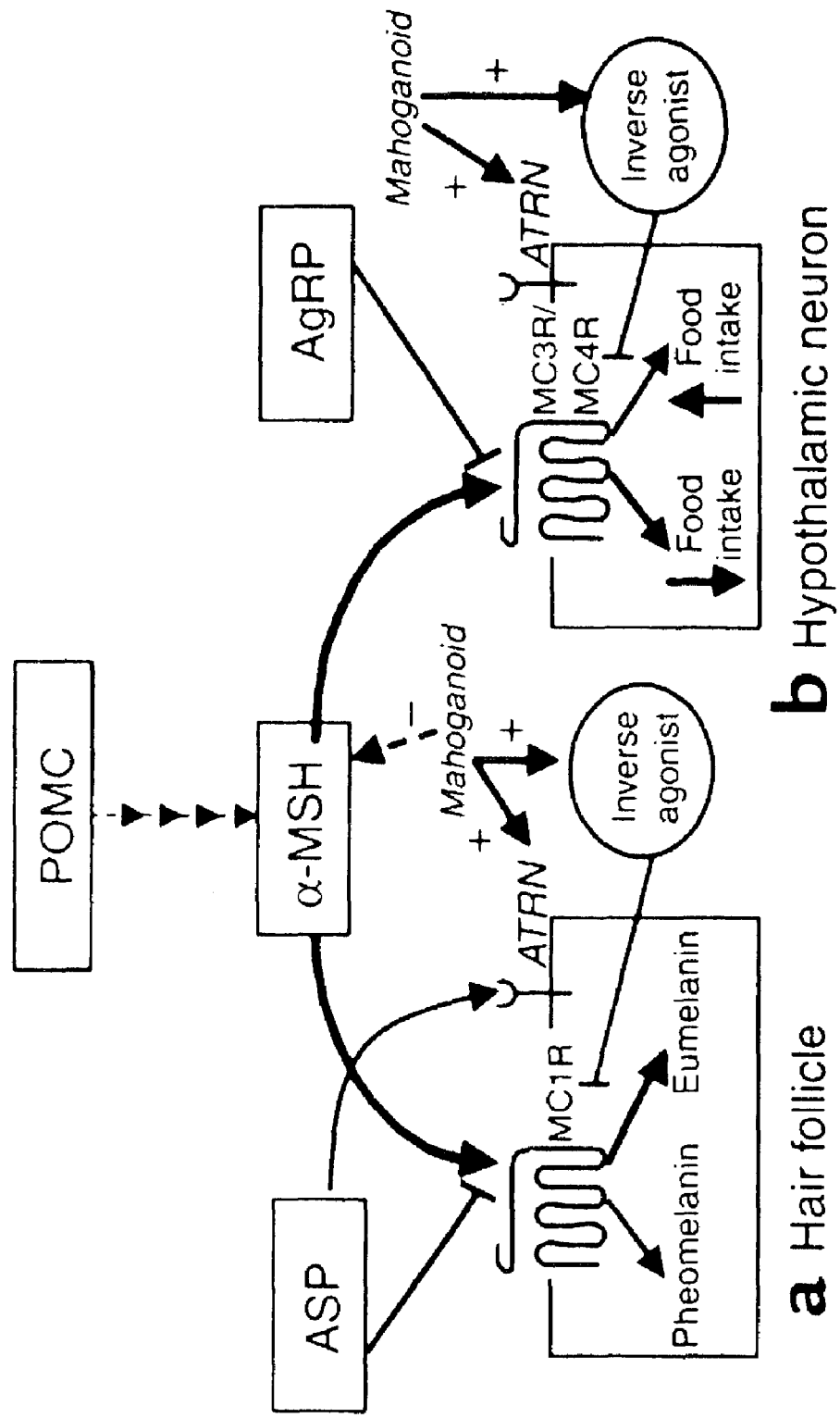

The mahoganoid protein may decrease signaling through MC1R and MC3R/MC4R by increasing expression or activity of an inverse agonist of MC1R and MC3R/MC4R, influencing the physical proximity or binding of ASP and AgRP to their receptors by influencing binding of ATRN to ASP or by decreasing the amount of α-MSH available to MC1R or MC3R/MC4R through sequestration or turnover of α-MSH (FIG. 9). If mahoganoid is an E3 ligase, identification of the targets of mahoganoid ubiquitylation should define additional components of this system. In this context, it should be noted that knockout mice lacking E3 ubiquitin ligase UBR1 activity have decreased body weight due to reduction in both skeletal muscle and adipose tissues (38). This phenotype supports a role for the E3 ligase in regulating body mass and composition.

The human homolog of mahoganoid maps to 16p13.3. Loci for coronary heart disease, hypertension, and type 2 diabetes have been mapped to this region in Indo-Mauritians and Pondicherian families of Indian origin (39). These phenotypes could be related to allelic variation in mahoganoid. This possibility can now be tested by mutation analysis and association studies.

REFERENCES

1. Leibel, R. L., Chung, W. K. and Chua, S. C. J. (1997). The molecular genetics of rodent single gene obesities. *J Biol Chem.* 272:31937-31940.
2. Bultman, S. J., Michaud, E. J. and Woychik, R. P. (1992). Molecular characterization of the mouse agouti locus. *Cell* 71:1195-1204.
3. Miller, M. W., Duhl, D. M., Vrieling, H., Cordes, S. P., Ollmann, M. M., Winkes, B. M. and Barsch, G. S. (1993). Cloning of the mouse agouti gene predicts a secreted protein ubiquitously expressed in mice carrying the lethal yellow mutation. *Genes Dev.* 7:454-467.
4. Michaud, E. J., Bultman, S. J., Klebig, M. L., van Bugt, M. J., Stubbs, L. J., Russell, L. B. and Woychik, R. P. (1994). A Molecular Model for the Genetic and Phenotypic Characteristics of the Mouse Lethal Yellow (Ay) Mutation. *Proc Natl Acad Sci USA.* 91:2562-2566.
5. Wolff, G. L., Galbraith, D. B., Domon, O. E. and Row, J. M. (1978). Phaeomelanin synthesis and obesity in mice. Interaction of the viable yellow (Avy) and sombre (eso) mutations. *J Hered.* 69:295-298.
6. Nijenhuis, W., Oosterom, J. and Adan, R. (2001). AgRP (83-132) acts as an inverse agonist on the human melanocortin-4 receptor. *Molecular Endocrinology* 15:164-171.
7. Haskell-Luevano, C. and Monck, E. K. (2001). Agouti-related protein functions as an inverse agonist as a constitutively active brain melanocortin-4 receptor. *Regulatory Peptides* 99:1-7.
8. Ollmann, M. M., Wilson, B. D.-, Yang, Y. K., Kerns, J. A., Chen, Y., Gantz, I. and Barsh, G. S. (1997). Antagonism of central melanocortin receptors in vitro and in vivo by agouti-related protein. *Science* 278:135-138.
9. Nagle, D. L., McGrail, S. H., Vitale, J., Woolf, E. A., Dussault, B. J. J., DiRocco, L., Holmgren, L., Montagno, J., Bork, P., Huszar, D., et al. (1999). The mahogany protein is a receptor involved in suppression of obesity. *Nature* 398:148-152.
10. Gunn, T. M., Miller, K. A., He, L., Hyman, R. W., Davis, R. W., Azarani, A., Schlossman, S. F., Duke-Cohan, J. S. and Barsh, G. S. (1999). The mouse mahogany locus encodes a transmembrane form of human attractin. *Nature* 398:152-156.
11. Dinulescu, D. M., Fan, W., Boston, B. A., McCall, K., Lamoreux, M. L., Moore, K. J., Montagno, J. and Cone, R. D. (1998). Mahogany (mg) stimulates feeding and increases basal metabolic rate independent of its suppression of agouti. *Proc Natl Acad Sci USA* 95:12707-12712.
12. Gunn, T., Inui, T., Kitada, K., Ito, K., Wakamtsu, K., He, L., Bouley, D. M., Serikawa, T. and Barsch, G. S. (2001). Molecular and phenotypic Analysis of Attractin Mutant mice. *Genetics* 158:1683-1695.
13. Kuramoto, T., Kitada, K., Inui, I., Sasaki, Y. and Ito, K. (2001). Attractin/Mahogany/Zitter plays a critical role in myelination of the central nervous system. *Proc Natl Acad Sci USA* 98:559-564.
14. He, L., Gunn, T. M., Bouley, D. M., Lu, X. Y., Watson, S. J., Schlossman, S. F., Duke-Cohan, J. S. and Barsh, G. S. (2001). A biochemical function for attractin in agouti-induced pigmentation and obesity. *Nat Genet.* 27:40-47.
15. Lane, P. W. (1960). New mutants. *Mouse News Lett.* 22: 35.
16. Lane, P. W. and Green, M. C. (1960). Mahogany, a recessive color mutation in linkage group V of the mouse. *J. Hered.* 51:228-230.

17. Miller, K. A., Gunn, T. M., Carrasquillo, M. M., Lamoreux, M. L., Galbraith, D. B. and Barsh, G. S. (1997). Genetic studies of the mouse mutations mahogany and mahoganoid. *Genetics.* 146:1407-1415.
18. Green, M. C. (1989). *Genetic Variants and Strains of the Laboratory Mouse.* Oxford, Oxford Unviersity Press.
19. Roderick, T., Davisson, M. and Lane, P. (1976). Chromosome 16 and mahoganoid md. *Mouse News Lett.* 55:18.
20. Chung, W. K., Power-Kehoe, L., Chua, M., Chu, F., Aronne, L., Huma, Z., Sothern, M., Udall, J. N., Kahle, B. and Leibel, R. L. (1997). Exonic and intronic sequence variation in the human leptin receptor gene (LEPR). *Diabetes* 46:1509-1511.
21. Sambrook, J., Fritsch, E. F. and Maniatis, T. (1989). *Molecular Cloning: A Laboratory Manual*, Cold Spring Harbor Laboratory Press.
22. Pfaffl, M. W., Georgieva, M. T., Georgiev, P. I., Ontsouka, E., Hageleit, M. and Blum, J. W. (2002). Real-time RT-PCR quantification of insulin-like growth factor (IGF)-1, IGF-1 receptor, IGF-2, IGF-2 receptor, insulin receptor, growth hormone receptor, IGF-binding proteins 1,2 and 3 in the bovine species. *Domestic Animal Endocrinology* 22:91-102.
23. Roderick, T., Donahue, L., Samples, R., Kim, J. and Naggert, J. (2001). Mice with mutations in the mahogany gene atrn have cerebral spongiform changes. *J Neuropathol Exp Neurol* 60:724-730.
24. Venter, J. C., Adams, M. D., Myers, E. W., Li, P. W., Mural, R. J., Sutton, G. G., Smith, H. O., Yandell, M., Evans, C. A., Holt, R. A., et al. (2001). The sequence of the human genome. *Science* 291:1304-1351.
25. Lower, R. (1999). The pathogenic potential of endogenous retroviruses: facts and fantasies. *Trends in Microbiology* 7:350-356.
26. Nagase, T., Ishikawa, K., Miyajima, N., Tanaka, A., Kotani, H., Nomura, N. and Ohara, O. (1998). Prediction of the coding sequences of unidentified human genes. IX. The complete sequences of 100 new cDNA clones from brain which can code for large proteins in vitro. *DNA Research* 5:31-39.
27. Bahary, N., Siegel, D. A., Walsh, J., Zhang, Y., Leopold, L., Leibel, R. L., Proenca, R. and Friedman, J. M. (1993). Microdissection of proximal mouse chromosome 6: identification of RFLPs tightly linked to the ob mutation. *Mammalian Genome* 4:511-515.
28. Yeo, G. S. H., Farooqi, I. S., Challis, B. G., Jackson, R. S. and O'Rahilly, S. (2000). The role of melanocortin signalling in the control of body weight: evidence from human and murine genetic models. *QJM* 93:7-14.
29. Seperack, P. K., Mercer, J. A., Strobel, M. C., Copeland, N. G. and Jenkins, N. A. (1995). Retroviral sequences located within an intron of the dilute gene alter dilute expression in a tissue-specific manner. *EMBO J* 14:2326-2332.
30. Palmiter, R. D., Erickson, J. C., Hollopeter, G., Baraban, S. C. and Schwartz, M. W. (1998). Life without Neuropeptide Y. *Recent Prog Horm Res* 53:163-199.
31. Saurin, A. J., Borden, K. L. B., Boddy, M. N. and Freemont, P. S. (1996). Does this have a familiar RING? *TIBS* 21:208-214.
32. Borden, K. and Freemont, P. S. (1996). The RING finger domain: a recent example of a sequence-structure family. *Current Opinion Structure Biology* 6:395-401.
33. Zheng, N., Wang, P., Jeffrey, P. D. and Pavletich, N. P. (2000). Structure of a c-Cbl-UbcH7 Complex: RING domain function in ubiquitin-protein ligases. *Cell* 102:533-539.
34. Joazeiro, C. A. and Weissman, A. M. (2000). RING finger proteins: mediators of ubiquitin ligase activity. *Cell* 102:549-552.
35. Conaway, R. C., Brower, C. S. and Conaway, J. W. (2002). Emerging Roles of Ubiquitin in Transcription Regulation. *Science* 296:1254-1258.

---

What is claimed is:

1. An isolated human mahoganoid polypeptide comprising amino acids the sequence of which is set forth in SEQ ID NO:8.

2. A composition comprising the polypeptide of claim 1 and a pharmaceutically acceptable carrier.

* * * * *

SEQUENCE LISTING

<160> NUMBER OF SEQ ID NOS: 25

<210> SEQ ID NO 1
<211> LENGTH: 34
<212> TYPE: DNA
<213> ORGANISM: mouse

<400> SEQUENCE: 1
tgatattttt cctgcactgt gggaagccgc cccc        34

<210> SEQ ID NO 2
<211> LENGTH: 34
<212> TYPE: DNA
<213> ORGANISM: mouse

<400> SEQUENCE: 2
gaacgcgtcg aataacactg caccctaggc aggc        34

<210> SEQ ID NO 3
<211> LENGTH: 33
<212> TYPE: DNA
<213> ORGANISM: mouse

<400> SEQUENCE: 3
gagctgtgca ggttgggtgt gggaagccgc ccc    33

<210> SEQ ID NO 4
<211> LENGTH: 34
<212> TYPE: DNA
<213> ORGANISM: mouse

<400> SEQUENCE: 4
gaacgcgtcg aataacagtt gggggaggag tggg    34

<210> SEQ ID NO 5
<211> LENGTH: 34
<212> TYPE: DNA
<213> ORGANISM: mouse

<400> SEQUENCE: 5
gaggcactca atggtctgtg ggaagccgcc ccca    34

<210> SEQ ID NO 6
<211> LENGTH: 34
<212> TYPE: DNA
<213> ORGANISM: mouse

<400> SEQUENCE: 6
acgaacgcgt ctaataacaa tggtctacga gctg    34

<210> SEQ ID NO 7
<211> LENGTH: 494
<212> TYPE: PRT
<213> ORGANISM: mouse

<400> SEQUENCE: 7

```
Met Gly Gly Glu Lys Phe Asp Thr Pro His Pro Glu Gly Tyr Leu Phe
1               5                   10                  15

Gly Glu Asn Met Asp Leu Asn Phe Leu Gly Ser Arg Pro Val Gln Phe
            20                  25                  30

Pro Tyr Val Thr Pro Ala Pro His Glu Pro Val Lys Thr Leu Arg Ser
        35                  40                  45

Leu Val Asn Ile Arg Lys Asp Ser Leu Arg Leu Val Arg Tyr Lys Glu
    50                  55                  60

Asp Ala Asp Ser Pro Thr Glu Asp Gly Glu Lys Pro Arg Val Leu Tyr
65                  70                  75                  80

Ser Leu Glu Phe Thr Phe Asp Ala Asp Ala Arg Val Ala Ile Thr Ile
                85                  90                  95

Tyr Cys Gln Ala Val Glu Glu Leu Val Asn Gly Val Ala Val Tyr Ser
            100                 105                 110

Cys Lys Asn Pro Ser Leu Gln Ser Glu Thr Val His Tyr Lys Arg Gly
        115                 120                 125

Val Ser Gln Gln Phe Ser Leu Pro Ser Phe Lys Ile Asp Phe Ser Glu
    130                 135                 140

Trp Lys Asp Asp Glu Leu Asn Phe Asp Leu Asp Arg Gly Val Phe Pro
145                 150                 155                 160

Val Val Ile Gln Ala Val Val Asp Glu Gly Asp Val Val Glu Val Thr
                165                 170                 175

Gly His Ala His Val Leu Leu Ala Ala Phe Glu Lys His Val Asp Gly
            180                 185                 190

Ser Phe Ser Val Lys Pro Leu Lys Gln Lys Gln Ile Val Asp Arg Val
        195                 200                 205
```

```
Ser Tyr Leu Leu Gln Glu Ile Tyr Gly Ile Glu Asn Lys Asn Asn Gln
    210                 215                 220

Glu Thr Lys Pro Ser Asp Glu Asn Ser Asp Asn Ser Ser Glu Cys
225                 230                 235                 240

Val Val Cys Leu Ser Asp Leu Arg Asp Thr Leu Ile Leu Pro Cys Arg
                245                 250                 255

His Leu Cys Leu Cys Thr Ser Cys Ala Asp Thr Leu Arg Tyr Gln Ala
            260                 265                 270

Asn Asn Cys Pro Ile Cys Arg Leu Pro Phe Arg Ala Leu Leu Gln Ile
        275                 280                 285

Arg Ala Val Arg Lys Lys Pro Gly Ala Leu Ser Pro Ile Ser Phe Ser
290                 295                 300

Pro Val Leu Ala Gln Ser Val Asp His Asp Glu His Ser Ser Ser Asp
305                 310                 315                 320

Ser Ile Pro Pro Gly Tyr Glu Pro Ile Ser Leu Leu Glu Ala Leu Asn
                325                 330                 335

Gly Leu Arg Ala Val Ser Pro Ala Ile Pro Ser Ala Pro Leu Tyr Glu
            340                 345                 350

Glu Ile Thr Tyr Ser Gly Ile Ser Asp Gly Leu Ser Gln Ala Ser Cys
        355                 360                 365

Pro Leu Ala Gly Leu Asp Arg Ile Met Glu Ser Gly Leu Gln Lys Gly
370                 375                 380

Lys Thr Gln Ser Lys Ser Pro Asp Ser Thr Leu Arg Ser Pro Ser Phe
385                 390                 395                 400

Pro Ile His Glu Glu Asp Glu Lys Leu Ser Glu Asp Ser Asp Ala
                405                 410                 415

Pro Leu Pro Pro Ser Gly Val Glu Leu Val Leu Arg Glu Ser Ser Ser
            420                 425                 430

Pro Glu Ser Phe Gly Thr Glu Glu Gly Asp Glu Pro Ser Leu Lys Gln
        435                 440                 445

Gly Ser Arg Val Pro Ser Ile Asp Asp Val Leu Gln Asp Gly Ser Pro
450                 455                 460

Gln His His Gly Cys Ser Gln Pro Val Pro Ala Asp Ile Tyr Leu
465                 470                 475                 480

Pro Ala Leu Gly Pro Glu Ser Cys Ser Val Gly Ile Glu Glu
                485                 490

<210> SEQ ID NO 8
<211> LENGTH: 492
<212> TYPE: PRT
<213> ORGANISM: human

<400> SEQUENCE: 8

Met Gly Gly Glu Lys Phe Asp Thr Pro His Pro Glu Gly Tyr Leu Phe
1               5                   10                  15

Gly Glu Asn Met Asp Leu Asn Phe Leu Gly Ser Arg Pro Val Gln Phe
                20                  25                  30

Pro Tyr Val Thr Pro Ala Pro His Glu Pro Val Lys Thr Leu Arg Ser
            35                  40                  45

Leu Val Asn Ile Arg Lys Asp Ser Leu Arg Leu Val Arg Tyr Lys Asp
        50                  55                  60

Asp Ala Asp Ser Pro Thr Glu Asp Gly Asp Lys Pro Arg Val Leu Tyr
65                  70                  75                  80

Ser Leu Glu Phe Thr Phe Asp Ala Asp Ala Arg Val Ala Ile Thr Ile
                85                  90                  95
```

```
Tyr Cys Gln Ala Ser Glu Glu Phe Leu Asn Gly Arg Ala Val Tyr Ser
            100                 105                 110

Pro Lys Ser Pro Ser Leu Gln Ser Glu Thr Val His Tyr Lys Arg Gly
            115                 120                 125

Val Ser Gln Gln Phe Ser Leu Pro Ser Phe Lys Ile Asp Phe Ser Glu
            130                 135                 140

Trp Lys Asp Asp Glu Leu Asn Phe Asp Leu Asp Arg Gly Val Phe Pro
145                 150                 155                 160

Val Val Ile Gln Ala Val Val Asp Glu Gly Asp Val Val Glu Val Thr
                    165                 170                 175

Gly His Ala His Val Leu Leu Ala Ala Phe Glu Lys His Met Asp Gly
                    180                 185                 190

Ser Phe Ser Val Lys Pro Leu Lys Gln Lys Gln Ile Val Asp Arg Val
                    195                 200                 205

Ser Tyr Leu Leu Gln Glu Ile Tyr Gly Ile Glu Asn Lys Asn Asn Gln
            210                 215                 220

Glu Thr Lys Pro Ser Asp Asp Glu Asn Ser Asp Asn Ser Asn Glu Cys
225                 230                 235                 240

Val Val Cys Leu Ser Asp Leu Arg Asp Thr Leu Ile Leu Pro Cys Arg
                    245                 250                 255

His Leu Cys Leu Cys Thr Ser Cys Ala Asp Thr Leu Arg Tyr Gln Ala
            260                 265                 270

Asn Asn Cys Pro Ile Cys Arg Leu Pro Phe Arg Ala Leu Leu Gln Ile
            275                 280                 285

Arg Ala Val Arg Lys Lys Pro Gly Ala Leu Ser Pro Val Ser Phe Ser
290                 295                 300

Pro Val Leu Ala Gln Ser Leu Glu His Asp Glu His Ser Asn Ser Asp
305                 310                 315                 320

Ser Val Pro Pro Gly Tyr Glu Pro Ile Ser Leu Leu Glu Ala Leu Asn
                    325                 330                 335

Gly Leu Arg Ala Val Ser Pro Ala Ile Pro Ser Ala Pro Leu Tyr Glu
                    340                 345                 350

Glu Ile Thr Tyr Ser Gly Ile Ser Asp Gly Leu Ser Gln Ala Ser Cys
            355                 360                 365

Pro Leu Ala Ala Ile Asp His Ile Leu Asp Ser Ser Arg Gln Lys Gly
            370                 375                 380

Arg Pro Gln Ser Lys Ala Pro Asp Ser Thr Leu Arg Ser Pro Ser Ser
385                 390                 395                 400

Pro Ile His Glu Glu Asp Glu Glu Lys Leu Ser Glu Asp Val Asp Ala
                    405                 410                 415

Pro Pro Pro Leu Gly Gly Ala Glu Leu Ala Leu Arg Glu Ser Ser Ser
                    420                 425                 430

Pro Glu Ser Phe Ile Thr Glu Glu Val Asp Glu Ser Ser Ser Pro Gln
            435                 440                 445

Gln Gly Thr Arg Ala Ala Ser Ile Glu Asn Val Leu Gln Asp Ser Ser
            450                 455                 460

Pro Glu His Cys Gly Arg Gly Pro Pro Ala Asp Ile Tyr Leu Pro Ala
465                 470                 475                 480

Leu Gly Pro Asp Ser Cys Ser Val Gly Ile Asp Glu
                    485                 490

<210> SEQ ID NO 9
<211> LENGTH: 39
```

```
<212> TYPE: PRT
<213> ORGANISM: mouse

<400> SEQUENCE: 9

Cys Val Val Cys Leu Ser Asp Leu Arg Asp Thr Leu Ile Leu Pro Cys
1               5                   10                  15

Arg His Leu Cys Leu Cys Thr Ser Cys Ala Asp Thr Leu Arg Tyr Gln
            20                  25                  30

Ala Asn Asn Cys Pro Ile Cys
            35

<210> SEQ ID NO 10
<211> LENGTH: 39
<212> TYPE: PRT
<213> ORGANISM: human

<400> SEQUENCE: 10

Cys Val Val Cys Leu Ser Asp Leu Arg Asp Thr Leu Ile Leu Pro Cys
1               5                   10                  15

Arg His Leu Cys Leu Cys Thr Ser Cys Ala Asp Thr Leu Arg Tyr Gln
            20                  25                  30

Ala Asn Asn Cys Pro Ile Cys
            35

<210> SEQ ID NO 11
<211> LENGTH: 39
<212> TYPE: PRT
<213> ORGANISM: D. melanogaster

<400> SEQUENCE: 11

Cys Val Ile Cys Met Ser Glu Thr Arg Asp Thr Leu Ile Leu Pro Cys
1               5                   10                  15

Arg His Leu Cys Leu Cys Asn Ser Cys Ala Asp Ser Leu Arg Tyr Gln
            20                  25                  30

Ala Asn Asn Cys Pro Ile Cys
            35

<210> SEQ ID NO 12
<211> LENGTH: 39
<212> TYPE: PRT
<213> ORGANISM: C. elegans

<400> SEQUENCE: 12

Cys Ile Ile Cys Leu Ser Asp Ile Arg Asp Thr Val Ile Leu Pro Cys
1               5                   10                  15

Arg His Leu Cys Val Cys Ser Asn Cys Ala Asp Ser Leu Arg Tyr Lys
            20                  25                  30

His Asn Asn Cys Pro Ile Cys
            35

<210> SEQ ID NO 13
<211> LENGTH: 41
<212> TYPE: PRT
<213> ORGANISM: mouse

<400> SEQUENCE: 13

Cys Pro Ile Cys Leu Glu Glu Tyr Leu Lys Asp Pro Val Val Leu Pro
1               5                   10                  15

Cys Gly His Thr Phe Cys Arg Ser Cys Ile Arg Lys Trp Leu Glu Ser
            20                  25                  30
```

```
Ser Asn Ser Asn Thr Cys Pro Ile Cys
        35                  40
```

<210> SEQ ID NO 14
<211> LENGTH: 21
<212> TYPE: DNA
<213> ORGANISM: Artificial sequence
<220> FEATURE:
<223> OTHER INFORMATION: Probe/Primer

<400> SEQUENCE: 14
gatggggctt gagtccttag a                                              21

<210> SEQ ID NO 15
<211> LENGTH: 21
<212> TYPE: DNA
<213> ORGANISM: Artificial sequence
<220> FEATURE:
<223> OTHER INFORMATION: Probe/Primer

<400> SEQUENCE: 15
cctcagccca gcactttctc t                                              21

<210> SEQ ID NO 16
<211> LENGTH: 21
<212> TYPE: DNA
<213> ORGANISM: Artificial sequence
<220> FEATURE:
<223> OTHER INFORMATION: Probe/Primer

<400> SEQUENCE: 16
ggcaggtggg aacagatgag t                                              21

<210> SEQ ID NO 17
<211> LENGTH: 21
<212> TYPE: DNA
<213> ORGANISM: Artificial sequence
<220> FEATURE:
<223> OTHER INFORMATION: Probe/Primer

<400> SEQUENCE: 17
ccgtccgaga tgcctgagta g                                              21

<210> SEQ ID NO 18
<211> LENGTH: 21
<212> TYPE: DNA
<213> ORGANISM: Artificial sequence
<220> FEATURE:
<223> OTHER INFORMATION: Probe/Primer

<400> SEQUENCE: 18
ttgacactcc ccatcctgaa g                                              21

<210> SEQ ID NO 19
<211> LENGTH: 21
<212> TYPE: DNA
<213> ORGANISM: Artificial sequence
<220> FEATURE:
<223> OTHER INFORMATION: Probe/Primer

<400> SEQUENCE: 19
tcctggttgt tcttgttctc g                                              21

<210> SEQ ID NO 20
<211> LENGTH: 21
<212> TYPE: DNA

```
<213> ORGANISM: Artificial sequence
<220> FEATURE:
<223> OTHER INFORMATION: Probe/Primer

<400> SEQUENCE: 20
ccagtttccc tatgtcaccc c                                              21

<210> SEQ ID NO 21
<211> LENGTH: 21
<212> TYPE: DNA
<213> ORGANISM: Artificial sequence
<220> FEATURE:
<223> OTHER INFORMATION: Probe/Primer

<400> SEQUENCE: 21
atggatgggg aatgatggag a                                              21

<210> SEQ ID NO 22
<211> LENGTH: 21
<212> TYPE: DNA
<213> ORGANISM: Artificial sequence
<220> FEATURE:
<223> OTHER INFORMATION: Probe/Primer

<400> SEQUENCE: 22
tgtctcccat ctccttcagc c                                              21

<210> SEQ ID NO 23
<211> LENGTH: 21
<212> TYPE: DNA
<213> ORGANISM: Artificial sequence
<220> FEATURE:
<223> OTHER INFORMATION: Probe/Primer

<400> SEQUENCE: 23
ctgtgtcttg cccttctgta g                                              21

<210> SEQ ID NO 24
<211> LENGTH: 18
<212> TYPE: DNA
<213> ORGANISM: Artificial sequence
<220> FEATURE:
<223> OTHER INFORMATION: Probe/Primer

<400> SEQUENCE: 24
atcgctgcgc tggtcgtc                                                  18

<210> SEQ ID NO 25
<211> LENGTH: 18
<212> TYPE: DNA
<213> ORGANISM: Artificial sequence
<220> FEATURE:
<223> OTHER INFORMATION: Probe/Primer

<400> SEQUENCE: 25
gctctgggcc tcgtcacc                                                  18
```